(12) United States Patent
Bronk et al.

(10) Patent No.: US 6,576,749 B2
(45) Date of Patent: Jun. 10, 2003

(54) C-4"-SUBSTITUTED MACROLIDE DERIVATIVES

(75) Inventors: Brian Scott Bronk, Gales Ferry, CT (US); Takushi Kaneko, Guilford, CT (US); Michael Anthony Letavic, Mystic, CT (US); Hengmaio Cheng, East Lyme, CT (US); Edward Alan Glazer, Waterford, CT (US); Bingwei Vera Yang, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/084,279

(22) Filed: Feb. 26, 2002

(65) Prior Publication Data

US 2002/0156026 A1 Oct. 24, 2002

Related U.S. Application Data

(63) Continuation of application No. 09/424,211, filed as application No. PCT/IB98/00799 on May 25, 1998, now Pat. No. 6,407,074.
(60) Provisional application No. 60/049,980, filed on Jun. 11, 1997.

(51) Int. Cl.$^7$ .......................... C07H 1/00; C07H 17/08
(52) U.S. Cl. ........................................ 536/7.4; 536/18.5
(58) Field of Search ................................ 536/7.4, 18.5; 514/29

(56) References Cited

U.S. PATENT DOCUMENTS 4,963,531 A * 10/1990 Remington ............... 514/29
6,407,074 B1 * 6/2002 Bronk et al. .............. 514/29

OTHER PUBLICATIONS

J. Sutcliffe et al., "Detection of Erythromycin–Resistant Determinants By PCR," *Antimicrobial Agents and Chemotherapy*, 40(11), 2562–2566 (1996).

J.P. Sanford, et al., "The Sanford Guide To Antimicrobial Therapy," 26$^{th}$ Ed., *Antimicrobial Therapy, Inc.* (1996).

T.W. Greene, et al., "Protective Groups in Organic Synthesis," *J. Wiley & Sons* (1991).

* cited by examiner

Primary Examiner—Elli Peselev
(74) Attorney, Agent, or Firm—Paul H. Ginsburg; Lorraine B. Ling; Kohn & Associates, PLLC

(57) ABSTRACT

Compounds are of the formula:

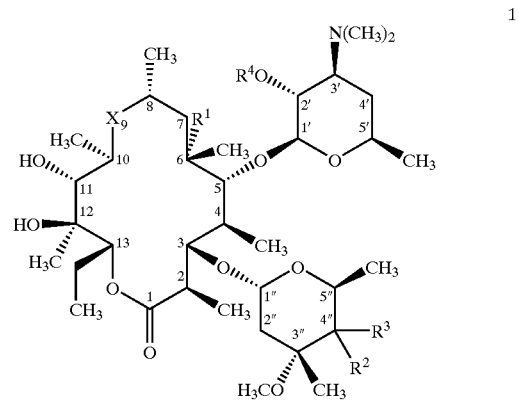

and to pharmaceutically acceptable salts thereof. The compounds of formula 1 are potent antibacterial agents that can be used to treat various bacterial infections and disorders related to such infections. The invention also relates to pharmaceutical compositions including the compounds of formula 1 and to methods of treating bacterial infections by administering the compounds of formula 1. The invention also relates to methods of preparing the compounds of formula 1 and to intermediates useful in such preparation.

4 Claims, No Drawings

C-4"-SUBSTITUTED MACROLIDE DERIVATIVES

BACKGROUND OF THE INVENTION

This invention relates to novel C-4" substituted macrolide derivatives that are useful as antibacterial and antiprotozoa agents in mammals, including man, as well as in fish and birds. This invention also relates to pharmaceutical compositions containing the novel compounds and to methods of treating bacterial and protozoa infections in mammals, fish and birds by administering the novel compounds to mammals, fish and birds requiring such treatment.

Macrolide antibiotics are known to be useful in the treatment of a broad spectrum of bacterial and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Like azithromycin and other macrolide antibiotics, the novel macrolide compounds of the present invention possess potent activity against various bacterial and protozoa infections as described below.

SUMMARY OF THE INVENTION

The present invention relates to compounds of the formula

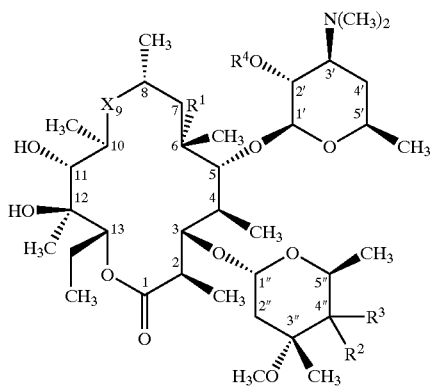

and to pharmaceutically acceptable salts thereof, wherein:

X is $-CH(NR^9R^{10})-$, $-C(O)-$, $-C(=NOR^9)-$, or $-N(C_1-C_8 \text{ alkyl})CH_2-$ wherein the first dash of each of the foregoing X groups is attached to the C-10 carbon of the compound of formula 1 and the last dash of each group is attached to the C-8 carbon of the of the compound of formula 1;

$R^1$ is H, hydroxy or methoxy;

$R^2$ is hydroxy;

$R^3$ is $C_1-C_{10}$ alkyl, $C_2-C_{10}$ alkenyl, $C_2-C_{10}$ alkynyl, cyano, $-CH_2S(O)_nR^8$ wherein n is an integer ranging from 0 to 2, $-CH_2OR^8$, $-CH_2N(OR^9)R^8$, $-CH_2NR^8R^{15}$, $-(CH_2)_m(C_6-C_{10} \text{ aryl})$, or $-(CH_2)m$ (5–10 membered heteroaryl), wherein m is an integer ranging from 0 to 4, and wherein the foregoing $R^3$ groups are optionally substituted by 1 to 3 $R^{16}$ groups;

or $R^2$ and $R^3$ are taken together to form an oxazolyl ring as shown below

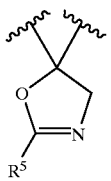

$R^4$ is H, $-C(O)R^9$, $-C(O)NR^9R^{10}$ or a hydroxy protecting group;

$R^5$ is $-SR^8$, $-(CH_2)_nC(O)R^8$ wherein n is 0 or 1, $C_1-C_{10}$ alkyl, $C_2-C_{10}$ alkenyl, $C_2-C_{10}$ alkynyl, $-(CH_2)_m(C_6-C_{10} \text{ aryl})$, or $-(CH_2)_m(5-10 \text{ membered heteroaryl})$, wherein m is an integer ranging from 0 to 4, and wherein the foregoing $R^5$ groups are optionally substituted by 1 to 3 $R^{16}$ groups;

each $R^6$ and $R^7$ is independently H, hydroxy, $C_1-C_6$ alkoxy, $C_1-C_6$ alkyl, $C_2-C_6$ alkenyl, $C_2-C_6$ alkynyl, $-(CH_2)_m(C_6-C_{10} \text{ aryl})$, or $-(CH_2)_m(5-10 \text{ membered heteroaryl})$, wherein m is an integer ranging from 0 to 4;

each $R^8$ is independently H, $C_1-C_{10}$ alkyl, $C_2-C_{10}$ alkenyl, $C_2-C_{10}$ alkynyl, $-(CH_2)_qCR^{11}R^{12}(CH_2)_rNR^{13}R^{14}$ wherein q and r are each independently an integer ranging from 0 to 3 except q and r are not both 0, $-(CH_2)_m(C_6-C_{10} \text{ aryl})$, or $-(CH_2)_m(5-10 \text{ membered heteroaryl})$, wherein m is an integer ranging from 0 to 4, and wherein the foregoing $R^8$ groups, except H, are optionally substituted by 1 to 3 $R^{16}$ groups;

or where $R^8$ is as $-CH_2NR^8R^{15}$, $R^{15}$ and $R^8$ may be taken together to form a 4–10 membered saturated monocyclic or polycyclic saturated ring or a 5–10 membered heteroaryl ring, wherein said saturated and heteroaryl rings optionally include 1 or 2 heteroatoms selected from O, S and $-N(R^8)-$, in addition to the nitrogen to which $R^{15}$ and $R^8$ are attached, said saturated ring optionally includes 1 or 2 carbon-carbon double or triple bonds, and said saturated and heteroaryl rings are optionally substituted by 1 to 3 $R^{16}$ groups;

each $R^9$ and $R^{10}$ is independently H or $C_1-C_6$ alkyl;

each $R^{11}$, $R^{12}$, $R^{13}$ and $R^{14}$ is independently selected from H, $C_1-C_{10}$ alkyl, $-(CH_2)_m(C_6-C_{10} \text{ aryl})$, and $-(CH_2)_m$ m(5–10 membered heteroaryl), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form $-(CH_2)_p-$ wherein p is an integer ranging from 0 to 3 such that a 4–7 membered saturated ring is formed that optionally includes 1 or 2 carbon—carbon double or triple bonds;

or $R^{13}$ and $R^{14}$ are taken together to form a 4–10 membered monocyclic or polycyclic saturated ring or a 5–10 membered heteroaryl ring, wherein said saturated and heteroaryl rings optionally include 1 or 2 heteroatoms selected from O, S and $-N(R^8)-$, in addition to the nitrogen to which $R^{13}$ and $R^{14}$ are attached, said saturated ring optionally includes 1 or 2 carbon—carbon double or triple bonds, and said saturated and heteroaryl rings are optionally substituted by 1 to 3 $R^{16}$ groups;

$R^{15}$ is H, $C_1-C_{10}$ alkyl, $C_2-C_{10}$ alkenyl, or $C_2-C_{10}$ alkynyl, wherein the foregoing $R^{15}$ groups are optionally substituted by 1 to 3 substituents independently selected from halo and $-OR^9$;

each $R^{16}$ is independently selected from halo, cyano, nitro, trifluoromethyl, azido, —C(O)$R^{17}$, —C(O)O$R^{17}$, —C(O)O$R^{17}$, —OC(O)O$R^{17}$, —N$R^6R^7$, —N$R^6R^7$, hydroxy, $C_1$–$C_6$ alkyl, $C_1$–$C_6$ alkoxy, —(CH$_2$)$_m$(C$_6$–C$_{10}$ aryl), and —(CH$_2$)$_m$(5–10 membered heteroaryl), wherein m is an integer ranging from 0 to 4, and wherein said aryl and heteroaryl substituents are optionally substituted by 1 or 2 substituents independently selected from halo, cyano, nitro, trifluoromethyl, azido, —C(O)$R^{17}$, —C(O)O$R^{17}$, —C(O)O$R^{17}$, —OC(O)O$R^{17}$, —N$R^6$C(O)$R^7$, —C(O)N$R^6R^7$, —N$R^6R^7$, hydroxy, $C_1$–$C_6$ alkyl, and $C_1$–$C_6$ alkoxy;

each $R^{17}$ is independently selected from H, $C_1$–$C_{10}$ alkyl, $C_2$–$C_{10}$ alkenyl, $C_2$–$C_{10}$ alkynyl, —(CH$_2$)$_m$(C$_6$–C$_{10}$ aryl), and —(CH$_2$)$_m$(5–10 membered heteroaryl), wherein m is an integer ranging from 0 to 4;

with the proviso that $r^8$ is not H where $R^3$ is —CH$_2$S(O)$_n$R$^8$.

Preferred compounds of formula 1 include those wherein $R^1$ is hydroxy, $R^2$ is hydroxy, $R^3$ is —CH$_2$NR$^8$R$^{15}$ or —CH$_2$SR$^8$, and $R^4$ is H.

Other preferred compounds of formula 1 include those wherein $R^1$ is hydroxy, $R^2$ is hydroxy, $R^3$ is —CH$_2$NR$^8$R$^{15}$, $R^4$ is H, $R^{15}$ and $R^8$ are each selected from H, $C_1$–$C_{10}$ alkyl, $C_2$–$C_{10}$ alkenyl, and $C_2$–$C_{10}$ alkynyl, wherein said $R^{15}$ and $R^8$ groups, except H, are optionally substituted by 1 or 2 substituents independently selected form hydroxy, halo and $C_1$–$C_6$ alkoxy. Specific preferred compounds having the foregoing general structure include those wherein $R^{15}$ is either H or is selected from the following groups from which $R^8$ is also independently selected: methyl, ethyl, allyl, n-butyl, isobutyl, 2-methoxyethyl, cyclopentyl, 3-methoxypropyl, 3-ethoxypropyl, n-propyl, isopropyl, 2-hydroxyethyl, cyclopropyl, 2,2,2-trifluoroethyl, 2-propynyl, sec-butyl, tert-butyl, and n-hexyl.

Other preferred compounds of formula 1 include those wherein $R^1$ is hydroxy, $R^2$ is hydroxy, $R^3$ is —CH$_2$NHR$^8$, $R^4$ is H, and $R^8$ is —(CH$_2$)$_m$(C$_6$–C$_{10}$ aryl) wherein m is an integer ranging from 0 to 4. Specific preferred compounds having the foregoing general structure include those wherein $R^8$ is phenyl or benzyl.

Other preferred compounds of formula 1 include those wherein $R^1$ is hydroxy, $R^2$ is hydroxy, $R^3$ is —CH$_2$NR$^{15}$R$^8$, $R^4$ is H, and $R^{15}$ and $R^8$ are taken together to form a saturated ring. Specific preferred compounds having the foregoing general structure include those wherein $R^{15}$ and $R^8$ are taken together to form a piperidino, trimethyleneimino, or morpholino ring.

Other preferred compounds of formula 1 include those wherein $R^1$ is hydroxy, $R^2$ is hydroxy, $R^3$ is —CH$_2$NR$^{15}$ R$^8$, $R^4$ is H, and $R^{15}$ and $R^8$ are taken together to form a heteroaryl ring optionally substituted by 1 or 2 $C_1$–$C_6$ alkyl groups. Specific preferred compounds having the foregoing general structure include those wherein $R^{15}$ and $R^8$ are taken together to form a pyrrolidino, triazolyl, or imidazolyl ring wherein said heteroaryl groups are optionally substituted by 1 or 2 methyl groups.

Other preferred compounds of formula 1 include those wherein $R^1$ is hydroxy, $R^2$ is hydroxy, $R^3$ is —CH$_2$SR$^8$, $R^4$ is H, and $R^8$ is selected from $C_1$–$C_{10}$ alkyl, $C_2$–$C_{10}$ alkyenyl, and $C_2$–$C_{10}$ alkynyl, wherein said $R^8$ groups are optionally substituted by 1 or 2 substituents independently selected from hydroxy, halo and $C_1$–$C_6$ alkoxy. Specific preferred compounds having the foregoing general structure include those wherein $R^8$ is methyl, ethyl, or 2-hydroxyethyl.

Other preferred compounds of formula 1 include those wherein $R^1$ is hydroxy, $R^2$ is hydroxy, $R^4$ is H, and $R^3$ is selected from $C_1$–$C_{10}$ alkyl, $C_2$–$C_{10}$ alkenyl, and $C_2$–$C_{10}$ alkynyl, wherein said $R^3$ groups are optionally substituted by 1 or 2 substituents independently selected from hydroxy, —C(O)$R^{17}$, —N$R^6R^7$, halo, cyano, azido, 5–10 membered heteroaryl, and $C_1$–$C_6$ alkoxy. Specific preferred compounds having the foregoing general structure include those wherein $R^3$ is methyl, allyl, vinyl, ethylyl, 1-methyl-1-propenyl, 3-methoxy-1-propynyl, 3-dimethylamino-1-propynyl, 2-pyridylethynyl, 1-propynyl, 3-hydroxy-1-propynyl, 3-hydroxy-1-propenyl, 3-hydroxypropyl, 3-methoxy-1propenyl, 3-methoxypropyl, 1-propynyl, n-butyl, ethyl, propyl, 2-hydroxyethyl, formylmethyl, 6-cyano-1-pentynyl, 3-dimethylamino-1-propenyl, or 3-dimethylaminopropyl.

Other preferred compounds of formula 1 include those wherein $R^1$ is hydroxy, $R^2$ is hydroxy, $R^4$ is H, and $R^3$ is —(CH$_2$)$_m$(5–10 membered heteroaryl) wherein m is an integer ranging from 0 to 4. Specific preferred compounds having the foregoing general structure include those wherein $R^3$ is 2-thienyl, 2-pyridyl, 1-methyl-2-imidazolyl, 2-furyl, or 1-methyl-2-pyrrolyl.

Other preferred compounds of formula 1 include those wherein $R^1$ is hydroxy, $R^2$ is hydroxy, $R^4$ is H, and $R^3$ is —(CH$_2$)$_m$(C$_6$–C$_{10}$ aryl) wherein m is an integer ranging from 0 to 4. Specific preferred compounds having the foregoing general structure include those wherein $R^3$ is phenyl.

Specific compounds of formula 1 include those wherein $R^2$ and $R^3$ are taken together to form an oxazolyl ring as shown below.

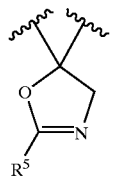

wherein $R^5$ is as defined above.

Specific compounds of formula 1 include those wherein $R^3$ is selected from the following:

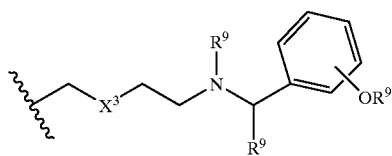

wherein $X^3$ is O, S or —N($R^{15}$)—, and wherein —O$R^9$ group may be attached at any available carbon on the phenyl group.

The invention also relates to a pharmaceutical composition for the treatment of a bacterial infection or a protozoa infection in a mammal, fish, or bird which comprises a therapeutically effective amount of a compound of formula 1, or a pharmaceutically acceptable salt thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula 1 or a pharmaceutically acceptable salt thereof.

The term "treatment", as used herein unless otherwise indicated, includes the treatment or prevention of a bacterial infection or protozoa infection as provided in the method of the present invention.

As used herein, unless otherwise indicated, the terms "bacterial infection(s)" and "protozoa infection(s)" include bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections, and disorders related to such infections, include the following: pneumonia, otitis media, sinusitus, bronchitis, tonsilitis, and mastoiditis related to infection by *Streptococcus pneumoniae, Haemonphilus influenzae, Moraxella catarrhalis, Staphylococcus aureus*, or *Peptostreptococcus* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus saprophyticus* or Enterococcus spp.; urethritis and cervicitis; and sexually transmitted diseases related to infection by *Chlamydia trachomatic, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis related to infection by *Helicobacter pylori* or *Chlamydia pneumoniae*. bacterial infections and protozoa infections and disorders related to such infections that may be treated or prevented in animals include the following: bovine respiratory disease related to infection by *P. haem., P. multocida, Mycoplasma bovis*, or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or Serpulina hyodyisinteriae; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius, coagulase neg. Staph.* or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et. al., "The Sanford Guide To Antimicrobial Therapy," 26th Edition, (Antimicrobial Therapy, Inc., 1996).

The present invention also relates to a method of preparing the above compound of formula 1, or a pharmaceutically acceptable salt thereof, wherein $R^3$ is —$CH_2S(O)_nR^8$, —$CH_2OR^8$ or —$CH_2NR^8R^{15}$, wherein n, $R^{15}$ and $R^8$ are as defined above with the proviso that $R^8$ is not H where $R^3$ is —$CH_2S(O)_nR^8$, which comprises treating a compound of the formula

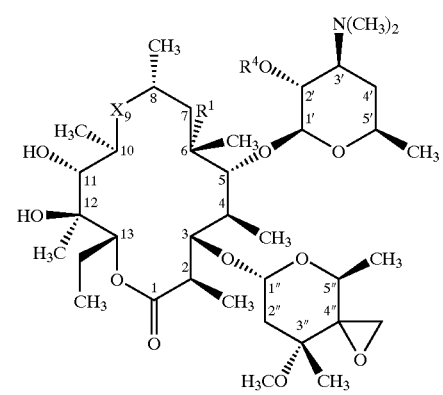

3 wherein X, $R^1$ and $R^4$ are as defined above, with a compound of the formula $HSR^8$, $HOR^8$ or $HNR^{15}R^8$, wherein n, $R^{15}$ and $R^8$ are as defined above, optionallly followed by oxidation of the —$SR^8$ substituent to form —$S(O)R^8$ or —$S(O)_2R^5$.

In a further aspect of the above process of preparing the compound of formula 1, or a pharmaceutically acceptable salt thereof, the above compound of formula 3 is prepared by treating a compound of the formula.

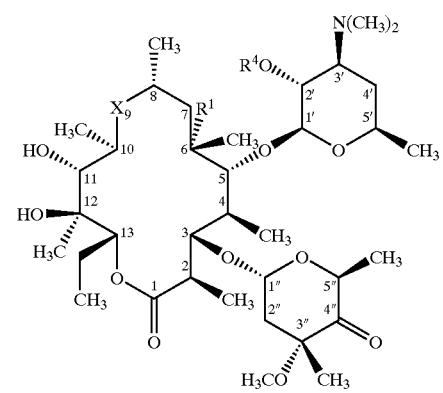

2 wherein X, $R^1$ and $R^4$ are as defined above, with $(CH_3)_3S(O)_nX^2$, wherein n is 0 or 1 and $X^2$ is halo, —$BF_4$ or —$PF_8$, preferably iodo or —BF$_4$, in the presence of a base such as as potassium tert-butoxide, sodium tert-butoxide, sodium ethoxide, sodium hydride, 1,1,3,3-tetramethyguanidine, 1,8-diazabicyclo[5.4.0]undec-7-ene, 1,5-diazabicylo[4.3.0]non-5-ene, potassium hexamethyldisilazide (KHMDS), potassium ethoxide, or sodium methoxide, preferably KHMDS or a sodium-containing base such as sodium hydride.

The present invention also relates to the above compounds of formulas 2 and 3 which, as indicated above, are useful in the preparation of the above compounds of formula 1 and pharmaceutically acceptable salts thereof.

The term "hydroxy protecting group", as used herein, unless otherwise indicated, includes acetyl, benzyloxycarbonyl, and various hydroxy protecting groups familiar to those skilled in the art including the groups referred to in T. W. Greene, P. G. M. Wuts, "Protective Groups in Organic Synthesis," (J. Wiley & Sons, 1991).

The term "halo", as used herein, unless otherwise indicated, includes fluoro, chloro bromo or iodo.

The term "alkyl", as used herein, unless otherwise indicated, includes saturated monovalent hydrocarbon radicals having straight, cyclic or branched moieties, or mixtues thereof. It is to be understood that where cyclic moieties are intended, at least three carbons in said alkyl must be present. Such cyclic moieties include cyclopropyl, cyclobutyl and cyclopentyl.

The term "alkoxy", as used herein, unless otherwise indicated, includes —O—alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "5–10 membered heteroaryl", as used herein, unless otherwise indicated, includes aromatic heterocyclic groups containing one or more heteroatoms each selected from O, S and N, wherein each heterocyclic group has from 5 to 10 atoms in its ring system. Examples of suitable 5–10 membered heteroaryl groups include pyridinyl, imidazolyl, pyrimidinyl, pyrazolyl, (1,2,3)— and (1,2,4—triazolyl, pyrazinyl, tetrazolyl, furyl, thienyl, isoxazolyl, oxazolyl, pyrrolyl and thiazolyl.

The phase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and parnoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of of the present invention may be prepared according to Schemes 1–3 below and the description that follows. In the following Schemes, unless otherwise indicated, substituents X, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined above.

Scheme 1

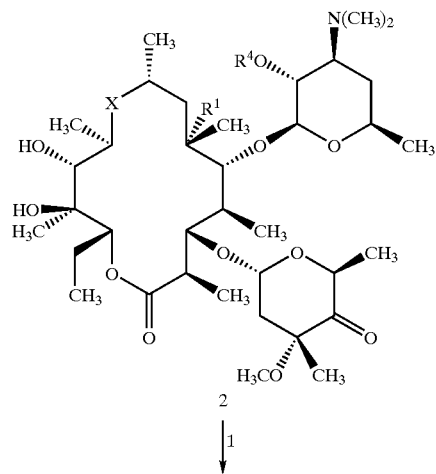

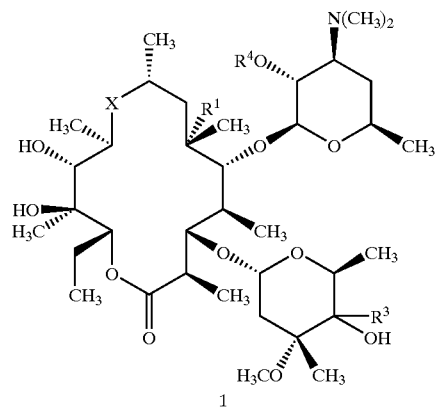

Scheme 2
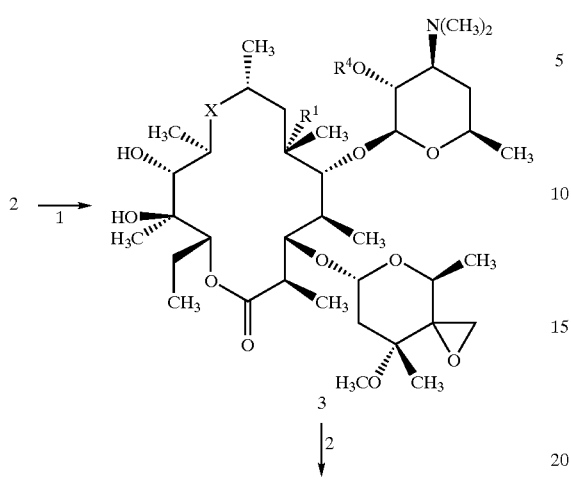
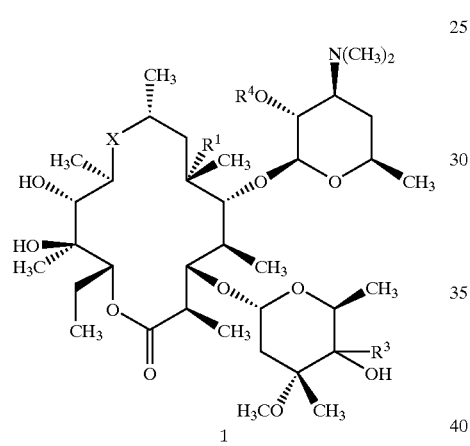
Scheme 3
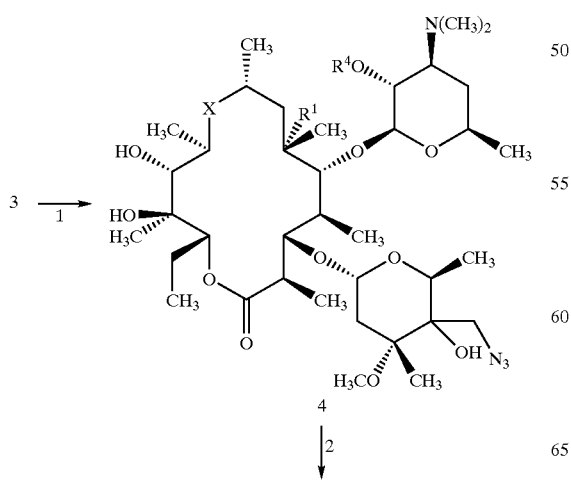
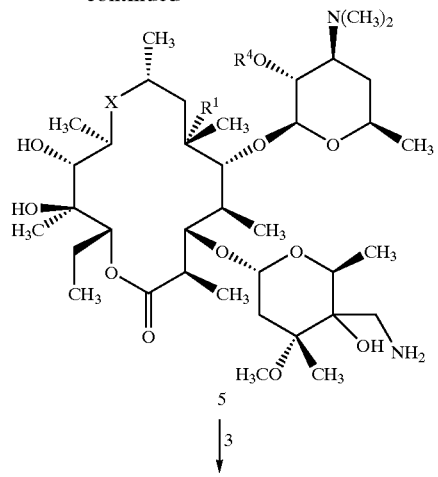
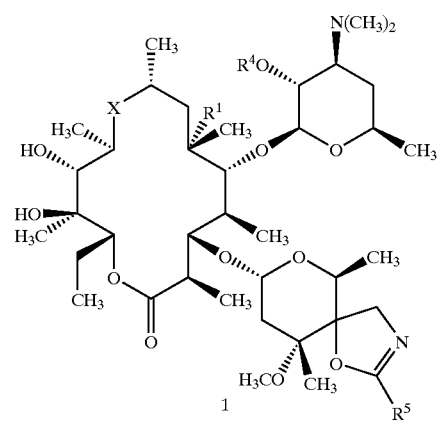
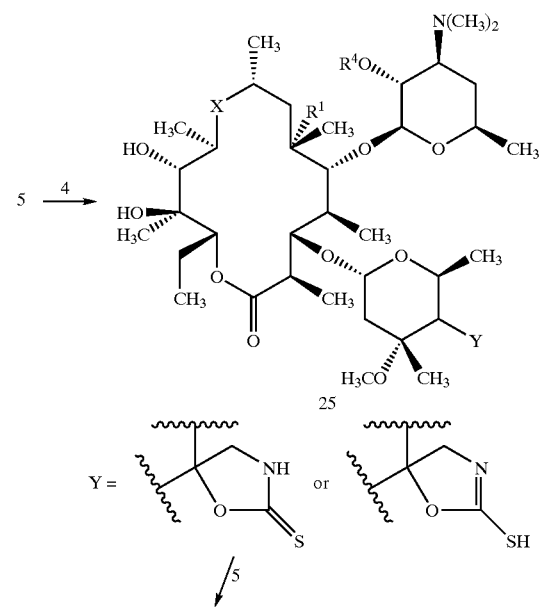

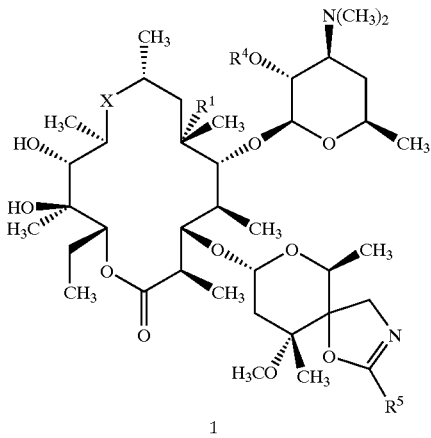

1

This invention uses a variety of macrolide templates as starting materials. They include azithromycin, erythromycin, clarithromycin, erythromycylamine as well as their analogs. Azithromycin can be prepared according to methods described in U.S. Pat. Nos. 4,474,768 and 4,517,359, referred to above. Erythromycin can be prepared, or isolated, according to methods described in U.S. Pat. Nos. 2,653,899 and 2,823,203. Clarithromycin can be prepared according to methods described in U.S. Pat. No. 4,331,803.

The foregoing starting materials require proper functional group protection before various modifications can take place, and deprotection after desired modifications are complete. The most commonly used protecting groups for amino moieties in the macrolide compounds of this invention are benzyloxycarbonyl (Cbz) and t-butyloxycarbonyl (Boc) groups. Hydroxyl groups are generally protected as acetates or Cbz carbonates. The relative reactivity of various hydroxyl groups in the macrolide molecules of the general type claimed in this invention has been well established. Such differences in reactivity permit selective modification of different parts of the compounds of this invention.

In above Schemes, the C-2' hydroxy group ($R^4$ is H) is selectively protected by treating the macrolide compound with one equivalent of acetic anhydride in dichloromethane in the absence of external base to provide the corresponding compound wherein $R^4$ is acetyl. The acetyl protecting group may be removed by treating the compound of formula 3 with methanol at 23–65° C. for 10–48 hours. The C-2' hydroxy may also be protected with other protecting group familiar to those skilled in the art, such as the Cbz group. Where X is —$CH_2NH$—, the C-9 amino group may also require protection before further synthetic modifications are performed. Suitable protecting groups for the amino moiety are Cbz and Boc groups. To protect the C-9 amino group, the macrolide may be treated with t-butyl dicarbonate in anhydrous tetrahydrofuran (THF) or benzylchloroformate in THF and water. The Boc group may be removed by acid treatment and group as its t-butyl or benzyl carbamate. Both the C-9 amino and C-2' hydroxy may be selectively protected with the Cbz group in one step by treating the compound of formula 2 with benzylchloromate in THF and water. The Boc group may be removed by acid treatment and the Cbz group may be removed by conventional catalytic hydrogenation. In the following description, it is assumed that, where X is —$CH_2NH$—, the C-9 amino moiety as well as the C-2' hydroxy group are protected and deprotected as would be deemed appropriate by those skilled in the art.

In Scheme 1, the compound of formula 2 may be prepared according to methods familiar to those skilled in the art, including one or more methods described in the Journal of Antibiotics, 1988, pages 1029–1047. In step 1 of Scheme 1, the compound of formula 2 is treated with $R^3MgX^1$ or $R^3$-Li and $Mg(X^1)_2$, wherein $X^1$ is a halide such as chloro or bromo, in a solvent such as THF, ethylene glycol dimethyl ether (DME), diisopropyl ether, toluene, diethyl ether, or tetramethylethylenediamine (TMEDA), hexanes, or a mixture of two or more of the foregoing solvents, preferably an ether solvent, at a temperature ranging from about −78° C. to about room temperature (20–25° C.), to provide the compound of formula 1 wherein $R^2$ is hydroxy and $R^1$, $R^3$ and $R^4$ are as defined above.

Scheme 2 illustrates the preparation of compounds of formula 1 through use of an epoxide intermediate. In step 1 of Scheme 2, the compound of formula 3 may be generated by two methods. In one method (Method A), the compound of formula 2 is treated with $(CH_3)_3S(O)X^2$, wherein $X^2$ is halo, —$BF_4$ or —$PF_6$, preferably iodo, in the presence of a base such as as potassium tert-butoxide, sodium ethoxide, sodium tert-butoxide, sodium hydride, 1,1,3,3-tetramethylguanidine, 1,8-diazabicyclo[5.4.0]undec-7-ene, 1,5-diazabicylo[4.3.0]non-5-ene, potassium ethoxide, or sodium methoxide, preferably a sodium-containing base such as sodium hydride, in a solvent such as THF, an ether solvent, dimethylformamide (DMF), or methyl sulfoxide (DMSO), or a mixture of two or more of the foregoing solvents, at a temperature within the range of about 0° C. to about 60° C., to provide the compound of formula 3 in which the following configuration of the epoxide moiety predominates

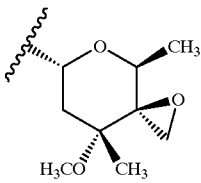

In a second method (Method B), the compound of formula 2 is treated with $(CH_3)_3SX^2$, wherein $X^2$ is halo, —$BF_4$ or —$PF_6$, preferably —$BF_4$, in the presence of a base such as as potassium tert-butoxide, sodium tert-butoxide, sodium ethoxide, sodium hydride, 1,1,3,3-tetramethylguanidine, 1,8-diazabicyclo[5.4.0]undec-7-ene, 1,5-diazabicyclo[4.3.0]non-5-ene, potassium ethoxide, potassium hexamethyldisilazide (KHMDS) or sodium methoxide, preferably KHMDS, in a solvent such as THF, an ether solvent, DMF, or DMSO, or a mixture of two or more of the foregoing solvents, at a temperature within the range of about 0° C. to about 60° C., to provide the compound of formula 3 in which the following configuration of the epoxide moiety predominates

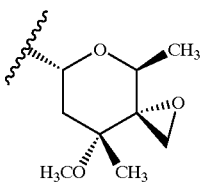

In step 2 of Scheme 2, the compound of formula 3 may be converted to a compound of formula 1 wherein $R^2$ is hydroxy and $R^3$ is a group that is attached to the C-4' carbon through a methylene group, such as where $R^3$ is —$CH_2NR^{15}R^8$ or —$CH_2S(O)_nR^8$ wherein n, $R^{15}$ and $R^8$ are as defined above. To prepare a compound of formula 1 wherein $R^3$ is —$CH_2NR^{15}R^8$, the compound of formula 3 may be treated with a compound of the formula $HNR^{15}R^8$, wherein $R^{15}$ and $R^8$ are as defined above, in the absence or presence of a polar solvent such as water, methanol, or THF, or a mixture of the foregoing solvents, at a temperature ranging from about room temperature to about 100° C., preferably about 60° C., optionally in the presence of a halide reagent such as potassium iodide, lithium perchlorate, magnesium perchlorate, lithium tetrafluoroborate, pyridinium hydrochloride, or a tetraalkylammonium halide reagent such as tetrabutylammonium iodide. To prepare a compound of formula 1 wherein $R^3$ is —$CH_2S(O)_nR^8$ wherein n and $R^8$ are as defined above, the compound of formula 3 may be treated with a compound of the formula $HSR^8$ in the presence of $K_2CO_3$, KI, or sodium methoxide, in an aromatic solvent such as methanol, benzene or toluene at a temperature ranging from about room temperature to about 120° C. As appropriate, the sulfur moiety may be oxidized to —SO— or —$SO_2$— according to methods familiar to those skilled in the art. To prepare a compound of formula 1 wherein $R^3$ is —$CH_2SR^8$ and $R^8$ is —$(CH_2)_9CR^{11}R^{12}(CH^2)_rNR^{13}R^{14}$, wherein the substituents of said $R^8$ group are as defined above, the compound of formula 3 may be treated with a compound of the formula HS—$(CH_2)_9CR^{11}R^{12}(CH_2)_r$NPhth, wherein NPhth represents phthalimido, and potassium iodide to provide the compound of formula 1 wherein $R^3$ is —$CH_2S(CH_2)_9CR^{11}R^{12}(CH_2)_rNH_2$, after removal of the phthalimido moiety, which may be further modified as necessary. By an analogous method, a compound of formula 1 wherein $R^3$ is —$CH_2NR^{15}R^8$ and $R^8$ is —$(CH_2)_9CR^{11}R^{12}(CH_2)_rNR^{13}R^{14}$ may be prepared by treating the compound of formula 3 with either a compound of the formula $HNR^9$-$(CH_2)_9CR^{11}R^{12}(CH_2)_r$-$NR^{13}R^{14}$ or a compound of the formula $H_2N$-$(CH_2)_9CR^{11}R^{12}(CH_2)_r$-$NH_2$ followed by reductive alkylation of the nitrogen atoms. Using the same or an analogous method, a compound of formula 1 wherein $R^3$ is —$CH_2OR^8$ and $R^8$ is as defined above may be prepared by treating a compound of formula 3 with a compound of the formula $HOR^8$.

Scheme 3 illustrates the preparation of compounds of formula 1 in which $R^2$ and $R^3$ are taken together to form an oxazolyl moiety. In step 1 of Scheme 3, the compound of formula 3 is treated with sodium azide in the presence of $NH_4Cl$ in methanol or water, or a mixture of the two solvents, at a temperature ranging from about 0° C. to about 100° C., preferably about 80° C., to provide the compound of formula 4. In step 2 of Scheme 3, the compound of formula 4 may be converted to the corresponding amine of formula 5 via conventional catalytic hydrogenation. Preferably, such hydrogenation is done using Pd (10% on carbon) powder under an $H_2$ atmosphere (1 atm). The resulting amine of formula 5 may be converted to various compounds of formula 1 wherein $R^3$ is —$CH_2NR^{15}R^8$ using conventional synthetic methods such as reductive amination.

In step 3 of Scheme 3, the compound of formula 5 may be converted to the compound of formula 1 wherein $R^2$ and $R^3$ are taken together as shown by treating the compound of formula 5 with a compound of formula $R^5$—CN, $R^5$—C=N(OCH_3), $R^5$—C=N(OC_2H_5), $R^5$—C(O)Cl, or $R^5$—$CO_2H$, wherein $R^5$ is as defined above, except it is not $NH_2$, in the presence or absence of an acid, such as Hcl, or a Lewis acid, such as $ZnCl_2$ or $BF_4Et_3O$, or a base, such as NaOH or TEA, in a solvent such as THF, a chlorohydrocarbon (such as $CH_2Cl_2$ or chlorobenzene), at a temperature ranging from about room temperature to reflux. To prepare the corresponding compound where $R^5$ is amino, the compound of formula 5 is treated with BrCN and sodium acetate in methanol at a temperature ranging from about room temperature to reflux. In the alternative, the compound of formula 5 may proceed as indicated in steps 4 and 5 of Scheme 3. In step 4 of Scheme 3, the compound of formula 5 is treated with thiocarbonyldiimidazole in methylene chloride at a temperature ranging from about 0° C. to room temperature to provide the compound of formula 25. In step 5 of Scheme 3, the compound of formula 25 is treated with $R^5$—$X^1$, wherein $X^1$ is a halide such as bromo or iodo, and a base such as sodium methoxide in a solvent such as methanol or acetone at a temperature ranging from about 0° C. to room temperature.

The compounds of the present invention may have asymmetric carbon atoms and therefore exist in different enantiomeric and diastereomers forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. Such separations may also be accomplished through use of standard chiral HPLC. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The antibacterial and antiprotozoa activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition: Approved Standard,* published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0065 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula 1, and the pharmaceutically acceptable salts thereof (hereinafter "the active compounds"), may be adminstered through oral, parenteral, topical, or rectal routes in the treatment of bacterial and protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidyicholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the method and intermediates of the present invention. It is to be understood that the present invention is not limited to the specific details of the Examples provided below.

TABLE 1

The compounds of Examples 1–18 have the general formula 6 below with the R substituents indicated in the table below. The compounds were prepared as described in Preparations 1–6 below. In the table, the yield and mass spectra ("Mass Spec") data apply to the final product.

| Example | R Substituent | Preparation | Yield | Mass Spec |
|---|---|---|---|---|
| 1 | n-butylamino | 1 | 67% | 835 |
| 2 | propylamino | 2 | 15% | 821 |
| 3 | methoxyethylamino | 1 | 27% | 836 |
| 4 | dimethylamino | 1 | 87% | 806 |
| 5 | cyclopropylamino | 1 | 59% | 818 |
| 6 | allylamino | 2 | 53% | 818 |
| 7 | imidazol-1-yl | 3 | 48% | 829 |
| 8 | 2,2,2-trifluoroethylamino | 2 | 19% | 860 |
| 9 | bis(2-hydroxyethyl)amino | 4 | 58% | 866 |
| 10 | bis(2-methoxyethyl)amino | 1 | 49% | 895 |
| 11 | 2-hydroxyethylthio | 5 | 83% | 840 |
| 12 | mercapto | 6 | 13% | 795 |
| 13 | 4-methylimidazol-1-yl | 3 | 45% | 843 |
| 14 | 2-propynylamino | 2 | 43% | 816 |
| 15 | diallylamino | 2 | 41% | 858 |
| 16 | 1,2,3-triazol-1-yl | 4 | 40% | 830 |
| 17 | 2-methylimidazol-1-yl | 3 | 21% | 843 |
| 18 | 1,2,4-triazol-1-yl | 4 | 67% | 835 |

PREPARATION METHODS FOR TABLE 1

Preparation 1

250–500 mg of the compound of formula 3 wherein X is —N(CH$_3$)CH$_2$—, R$^1$ is hydroxy, and R$^4$ is H, prepared in accord with Method A referred to above, was dissolved in 1–2 mL of an amine corresponding to the R groups indicated in Table 1 above. A catalytic amount (20 mg) of pyridinium hydrochloride was added and the solution was heated to 50–75° C. for approximately two to five days. The reaction was worked up by quenching with 50 mL saturated NaHCO$_3$. The organic layer was extracted with 3×50 mL CH$_2$Cl$_2$ and dried over Na$_2$SO$_4$. Filtration, concentration of the filtrate, and drying gave a crude oil or solid. Further purification on a silica gel column (1.5–4% MeOH/CHCl$_3$, 0.2% NH$_4$OH) afforded the final amino alcohol product.

Preparation 2

250–500 mg of the compound of formula 3 wherein X is —N(CH$_3$)CH$_2$—, R$^1$ is hydroxy, and R$^4$ is H, prepared in accord with Method A referred to above, was dissolved in 1–2 mL of an amine corresponding to the R groups indicated in Table 1 above in a sealed tube. A catalytic amount (20 mg) of pyridinium hydrochloride was added and the solution was heated to 40–75° C. for approximately four to eight days. The reaction was worked up by quenching with 50 mL saturated NaHCO$_3$. The organic layer was extracted with 3×50 mL CH$_2$Cl$_2$ and dried over Na$_2$SO$_4$. Filtration, concentration of the filtrate, and drying gave a crude oil or solid. Further purification on a silica gel column (1.5–4% MeOH/CHCl$_3$, 0.2% NH$_4$OH) afforded the final amino alcohol product.

Preparation 3

300 mg of the compound of formula 3 wherein X is —N(CH$_3$)CH$_2$—, R$^1$ is hydroxy, and R$^4$ is H, prepared in accord with Method A referred to above, was dissolved in 2–4 mL MeOH/H$_2$O. To this was added an imidazole reagent corresponding to the R groups indicated in Table 1 above (25 equiv) and a catalytic amount (20 mg) of pyridinium hydrochloride. The reaction mixture was refluxed at 45–50° C. for three to four days. The reaction was then quenched with saturated NaHCO$_3$, extracted with 3×300 mL CH$_2$Cl$_2$, dried over Na$_2$SO$_4$, filtered, and concentrated to a solid. The solid was redissolved in 500 mL EtOAc and washed with 3×150 mL 2N NaOH to remove the excess imidazole. Further purification on a silica gel column (2–4% MeOH/CHCl$_3$, 0.2% NH$_4$OH) afforded the final product.

Preparation 4

200–500 mg of the compound of formula 3 wherein X is —N(CH$_3$)CH$_2$—, R$^1$ is hydroxy, and R$^4$ is H, prepared in accord with Method A referred to above, was dissolved in 1–2 mL of 2-propanol or methanol. To this was added excess reagent and a catalytic amount (20 mg) of pyridinium hydrochloride. The solution was heated to 40–75° C. for approximately two to seven days. The reaction was concentrated down to a crude product. Further purification on a silica gel column (2–4% MeOH/CHCl$_3$, 0.2% NH$_2$OH) afforded the final amino alcohol product.

Preparation 5

180 mg of the compound of formula 3 wherein X is —N(CH$_3$)CH$_2$—, R$^1$ is hydroxy, and R$^4$ is H, prepared in accord with Method A referred to above, was dissolved in 2 mL benzene. To this was added excess K$_2$CO$_3$ and 0.5 mL of thiol. The mixture was stirred at room temperature for 16 hours. The reaction was quenched with 100 mL saturated NaHCO$_3$, extracted with 3×25 mL CH$_2$Cl$_2$, dried over Na$_2$SO$_4$, filtered, and concentrated to a solid. Further purification on a silica gel column (2%MeOH/CHCl$_3$, 0.2% NH$_4$OH) afforded the final product.

Preparation 6

115 mg of the compound of formula 3 wherein X is —N(CH$_3$)CH$_2$—, R$^1$ is hydroxy, and R$^4$ is H, prepared in accord with Method A referred to above, was dissolved in 3 mL ethanol. To this was added excess thiol. The mixture was heated to 50° C. for 4 hours. The reaction was quenched with 100 mL saturated NaHCO$_3$, extracted with 3×25 mL CH$_2$Cl$_2$, dried over Na$_2$SO$_4$, filtered, and concentrated to a solid. Further purification on a silica gel column (2–4% MeOH/CHCl$_3$, 0.2% NH$_4$OH) afforded the final product.

Examples 19–35 below describe the preparation of compounds having the general structure of formula 7 below wherein R is as defined in the examples.

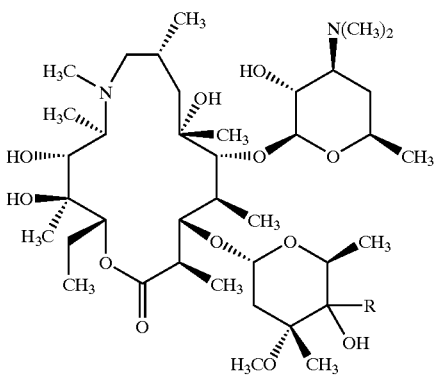

EXAMPLE 19

To a solution of methylmagnesium bromide in Et$_2$O (3.0 M, 1.7 mL) at 0° C. was added a solution of methyl propargyl ether (0.421 g, 6 mmol) in THF (5 mL). After stirring at 0° C. for 6 hours, a solution of 4"-deoxy-4"-oxo-9-deoxo-9a-aza-9a-methyl-9a-homoerythrnmycin A (0.224 g, 0.3 mmol) in DME (10 mL) was added at room temperature. After stirring for 1 hour, the reaction mixture was diluted with water (50 mL) and EtOAc (50 mL). After separation, the aqueous layer was washed with EtOAc (3×30 mL). The combined organic extracts were washed with a saturated aqueous solution of sodium bicarbonate (40 mL) and brine (40 mL), dried over Na$_2$SO$_4$ and concentrated under vacuum. Silica gel chromatography with MeOH—CH$_2$Cl$_2$—NH$_4$OH (6:93.5:0.5 to 8:91.5:0.5) afforded 0.0959 (39% yield) of the compound of formula 7 wherein R is 3-methoxy-1-propynyl: MS: 817 (API).

EXAMPLE 20

To a solution of methylmagnesium bromide in Et$_2$O (3.0 M, 1.7 mL) at 0° C. was added a solution of 1-dimethylamino-2-propyne (0.499 g, 6 mmol) in THF (5 mL). After stirring at 0° C. for 6 hours, a solution of 4"-deoxy-4"-oxo-9-deoxo-9a-aza-9a-methyl-9a-homoerythrnmycin A (0.224 g, 0.3 mmol) in DME (10 mL) was added at room temperature. After stirring at room temperature for 1 hour, the reaction mixture was diluted with water (50 mL) and EtOAc (40 mL). After separation, the aqueous layer was washed with EtOAc (3×30 mL). The combined organic extracts were washed with a saturated aqueous solution of sodium bicarbonate (40 mL) and brine (50 mL), dried over Na$_2$SO$_4$ and concentrated under vacuum. Silica gel chromatography with MeOH—CH$_2$Cl$_2$—NH$_4$OH (6:93.5:0.5 to 10:89.5:0.5) afforded 0.093 g (37% yield) of the compound of formula 7 wherein R is 3-dimethylamino-1-propynyl: MS: 831 (API).

EXAMPLE 21

To a suspension of trimethylsulfonium tetrafluoroborate (1.03 g, 6.3 mmol) in THF (40 mL) at −10° C. was added KHMDS (1.20 g, 6.0 mmol). After stirring below 0° C. for 0.5 hour, the reaction vessel was cooled to −78° C. and a solution of the compound of formula IV wherein X is —N(CH$_3$)CH$_2$— and R$^{13}$ is benzyloxycarboxy (2.60 g, 3 mmol) in DME (10 mL) was added. After 0.5 hour, the reaction mixture was diluted with a saturated aqueous solution of ammonium chloride (40 mL) and EtOAc (50 mL). After separation, the aqueous layer was washed with EtOAc (3×30 mL). The combined organic extracts were washed with brine (40 mL), dried over Na$_2$SO$_4$ and concentrated under vacuum. Silica gel chromatography with MeOH—CH$_2$Cl$_2$—NH$_4$OH (2:97.6:0.4 to 4:95.5:0.4) afforded 0.834 g (32% yield) of the compound of formula 3 wherein X is —N(CH$_3$)CH$_2$— and R$^{13}$ is benzyloxycarbonyl: MS: 881 (API). The configuration of the epoxide moiety was as provided for Method B relating to Scheme 2 above.

EXAMPLE 22

To a solution of the compound of Example 21 (0.101 g, 0.115) in DME (3 mL) was added LiAlH$_4$ (1.0 M, 2.1 mL) dropwise. After 10 minutes the reaction mixture was treated sequentially with water (0.044 mL), 15% NaOH solution (0.044 mL), and water (0.132 mL), then stirred at rt for 0.5 hour. The mixture was diluted with EtOAc (20 mL) and water (20 mL). After separation the aqueous layer was extracted with EtOAc (3×30 mL). The combined organic extracts were washed with a saturated aqueous solution of sodium bicarbonate (50 mL) and brine (60 mL), dried over Na$_2$SO$_4$ and concentrated under vacuum. Silica gel chromatography with MeOH—CH$_2$Cl$_2$—NH$_4$OH (3:96.5:0.5 to 3.5:95:0.5) afforded 0.042 g (49% yield) of an intermediate compound: MS: 749 (API).

Palladium catalyst (0.075 mg, 10% Pd/C) was added to a solution of the intermediate compound described above (0.151 g, 0.202 mmol) and formaldehyde (0.17 mL, 2.02 mmoL) in methanol (20 mL). The reaction vessel was flushed and filled with hydrogen (50 psi) and shaken at room temperature for 24 hours. The reaction mixture was filtered through Celite™ and concentrated under vacuum. Silica gel chromatography with hexanes—acetone—n-propanol—NH$_4$OH (100:10:3:0.5 to 50:10:3:0.5) afforded 0.098 g (64% yield) of 4"S-methyl-9-deoxo-9a-aza-9a-methyl-9a-homoerythromycin A: MS: 763 (API).

EXAMPLE 23

To a solution of 4"-deoxy-4"-oxo-9-deoxo-9a-aza-9a-methyl-9a-homoerythrnmycin A (1.0 g, 1.34 mmol) in DME (50 mL) at 0° C. was added ethynylmagnesium bromide in THF (0.5 M, 40.2 mL). After stirring at 0° C. for 0.5 hour the reaction mixture was diluted with a saturated aqueous solution of sodium bicarbonate (100 mL) and EtOAc (100 mL). After separation, the aqueous layer was washed with EtOAc (3×100 mL). The combined organic extracts were washed with a saturated aqueous solution of sodium bicarbonate (100 mL) and brine (100 mL), dried over Na$_2$SO$_4$ and concentrated under vacuum. Silica gel chromatography with MeOH—CH$_2$Cl$_2$—NH$_4$OH (4:95.5:0.5) afforded 0.089 g (9% yield) of the compound of formula 7 wherein R is ethynyl: MS: 774 (API).

EXAMPLE 24

To a solution of N-methylpyrrole (0.217 g, 2.68 mmol) in THF (5 ml) at −78° C. was added BuLi (2.5M, 1.08 ml). The solution was warmed to room temperature over 2 hours and then added via cannula to a flask containing MgCl$_2$ (0.38 g, 4.02 mmol) and THF (5 mL) at room temperature. After 1 hour at room temperature, a solution of 4"-deoxy-4"-oxo-9-deoxo-9a-aza-9a-methyl-9a-homoerythromycin A (0.200 g, 0.268 mmol) in THF (2 mL) was introduced and stirring was continued at room temperature for 45 minutes. The reaction mixture was diluted with a saturated aqueous solution of sodium bicarbonate (50 mL) and EtOAc (50 mL). After separation, the aqueous layer was washed with EtOAc (3×50 mL). The combined organic extracts were washed with a saturated aqueous solution of sodium bicarbonate (50 mL) and brine (50 mL), dried over $Na_2SO_4$ and concentrated under vacuum. Silica gel chromatography with MeOH—$CH_2Cl_2$—$NH_4OH$ (1:98:1 to 8:91:1) afforded 0.032 g (14% yield) of the compound of formula 7 wherein R is 1-methyl-2-pyrrolyl: MS: 829 (API).

EXAMPLE 25

To a solution of N-methylimidazole (0.440 g, 5.36 mmol) in THF (5 ml) at −78° C. was added BuLi (2.5M, 2.15 ml). The solution was warmed to room temperature over 1 hour and then added via cannula to a flask containing $MgCl_2$ (0.6374 g, 6.69 mmol) and THF (5 mL) at room temperature. After 2 hours at room temperature, a solution of 4"-deoxy-4"-oxo-9-deoxo-9a-aza-9a-methyl-9a-homoerythromycin A (0.200 g, 0.268 mmol) in DME (2 mL) was introduced and stirring was continued at room temperature for 45 minutes. The reaction mixture was diluted with a saturated aqueous solution of sodium bicarbonate (50 mL) and EtOAc (50 mL). After separation, the aqueous layer was washed with EtOAc (3×50 mL). The combined organic extracts were washed with a saturated aqueous solution of sodium bicarbonate (50 mL) and brine (50 mL), dried over $Na_2SO_4$ and concentrated under vacuum. Silica gel chromatography with MeOH—$CH_2Cl_2$—$NH_4OH$ (1:98:1 to 8:91:1) afforded 0.042 g (19% yield) of the compound of formula 7 wherein R is 1-methyl-2-imidazolyl: MS: 830 (API).

EXAMPLE 26

To a solution of an unpurified sample of the compound prepared in Example 20 (0.3609) in isopropanol (40 mL) was added platinum oxide (0.076 g, 0.335 mmol). The reaction vessel was flushed and filled with hydrogen (50 psi) and shaken at room temperature for 24 hours. Filtration of an aliquot of the reaction mixture through Celite™ and concentration under vacuum afforded the compound of formula 7 wherein R is 3-dimethylamino-1-propenyl: MS: 833 (API).

EXAMPLE 27

Platinum oxide (0.076 g, 0.335 mmol) was added to solution remaining from Example 26 and the reaction vessel was flushed and filled with hydrogen (50 psi) and shaken at room temperature for 96 hours. The reaction mixture was filtered through Celite™ and concentrated under vacuum. Silica gel chromatography with MeOH—$CH_2Cl_2$—$NH_4OH$ (1:98:1 to 8:91:1) afforded 0.027 g (5% yield) of the compound of formula 7 wherein R is 3-dimethylaminopropyl: MS: 835 (API).

EXAMPLE 28

To a solution of an unpurified sample of the compound prepared in Example 19 (0.400 g) in isopropanol (40 mL) was added platinum oxide (0.076 g, 0.335 mmol). The reaction vessel was flushed and filled with hydrogen (50 psi) and shaken at room temperature for 24 hours. Filtration of an aliquot of the reaction mixture through Celite™ and concentration under vacuum afforded the compound of formula 7 wherein R is 3-methoxy-1-propenyl: MS: 819 (API).

EXAMPLE 29

Platinum oxide (0.076 g, 0.335 mmol) was added to solution remaining from Example 26 and the reaction vessel was flushed and filled with hydrogen (50 psi) and shaken at room temperature for 96 hours. The reaction mixture was filtered through Celite and concentration under vacuum. Silica gel chromatography with MeOH—$CH_2Cl_2$—$NH_4OH$ (1:98:1 to 8:91:1) afforded 0.119 g (21% yield) of the compound of formula 7 wherein R is 3-methoxypropyl: MS: 822 (API).

EXAMPLE 30

To a flask containing $MgB_2.OEt_2$ (2.28 g, 8.84 mmol) in DME (5 mL) at 0° C. was added propynyllithium (1.865 g, 8.03 mmol). After 6 hours at 0° C., a solution of 4"-deoxy-4"-oxo-9deoxo-9a-aza-9a-methyl-9a-homoerythromycin A (0.300 g, 0.402 mmol) in DME (2 mL) was introduced and stirring was continued at 0° C. for 1 hour, then at room temperature for 0.5 hour. The reaction mixture was diluted with a saturated aqueous solution of sodium bicarbonate (75 mL) and EtOAc (75 mL). After separation, the aqueous layer was washed with EtOAc (3×75 mL). The combined organic extracts were washed with a saturated aqueous solution of sodium bicarbonate (75 mL) and brine (75 mL), dried over $Na_2SO_4$ and concentrated under vacuum. Silica gel chromatography with MeOH—$CH_2Cl_2$—$NH_4OH$ (1:98:1 to 8:91:1) afforded 0.099 g (31% yield) of the compound of formula 7 wherein R is 1-propynyl as a mixture of isomers: MS: 788 (API).

EXAMPLE 31

To a solution of 4"-deoxy-4"-oxo-9-deoxo-9a-aza-9a-methyl-9a-homoerythromycin A (0.59 g, 0.79 mmol) in THF (20 ml) was added a solution of MeMgBr in $Et_2O$ (1.7 ml, 5.1 mmol, 3.0 M $Et_2O$ solution) at 0° C. The slurry was stirred at 0° C. for one hour and was gradually warmed up to room temperature. After 3 hours, the reaction mixture was quenched with a saturated solution of $NH_4Cl$ (10 ml). The organic solvent was removed in vacuo on a rotary evaporator. The remaining aqueous solution was adjusted to pH 9.5 with a saturated solution of $NaHCO_3$ followed by addition of ethyl acetate (30 ml). The aqueous layer, after separation, was extracted with ethyl acetate (2×30 ml). The combined organic extracts were washed with brine, dried over magnesium sulfate and concentrated to afford the crude product. Chromatographic purification (silica gel with MeOH/$CHCl_3$/$NH_4OH$ (4:95.9:0.1) as eluents), provided 4"R-methyl-9-deoxo-9a-aza-9a-methyl-9a-homoerythromycin A (which is the compound of formula 7 wherein R is methyl having the R configuration specified) as a white solid, 240 mg (0.315 mmol, 40% yield): FABMS: m/e 763 ($MH^+$).

EXAMPLE 32

Following the procedure of Example 31, 4"-deoxy-4"-oxo-9-deoxo-9a-aza-9a-methyl-9a-homoerythromycin A (299 mg, 0.403 mmol) and phenyl magnesiumbromide (0.87 ml, 2.61 mmol, 3.0 M THF solution) were reacted to generate the compound of formula 7 wherein R is phenyl, 74 mg (0.09 mmol, 22% yield): FABMS: m/e 825 ($MH^+$).

EXAMPLE 33

Following the procedure of Example 31, 4"-deoxy-4"-oxo-9-deoxo-9a-aza-9a-methyl-9a-homoerythromycin A (482 mg, 0.646 mmol) and vinyl magnesiumbromide (4.2 ml, 4.2 mmol, 1.0 M THF solution) were reacted to generate the compound of formula 7 wherein R is vinyl, 133 mg (0.172 mmol, 26.6% yield): FABMS: m/e 774 (MH$^+$).

on silica gel with CHCl$_3$—MeOH—NH$_4$OH (97 : 3: 0.1) as eluents afforded the compound of formula 7 wherein R is cyano as a white solid, 94.4 mg (0.122 mmol, 15% yield): FABMS: m/e 774 (MH$^+$).

The following scheme illustrates the preparation of the components referred to in Table 2 below. In the following scheme, Cbz represents benzyloxycarbonyl

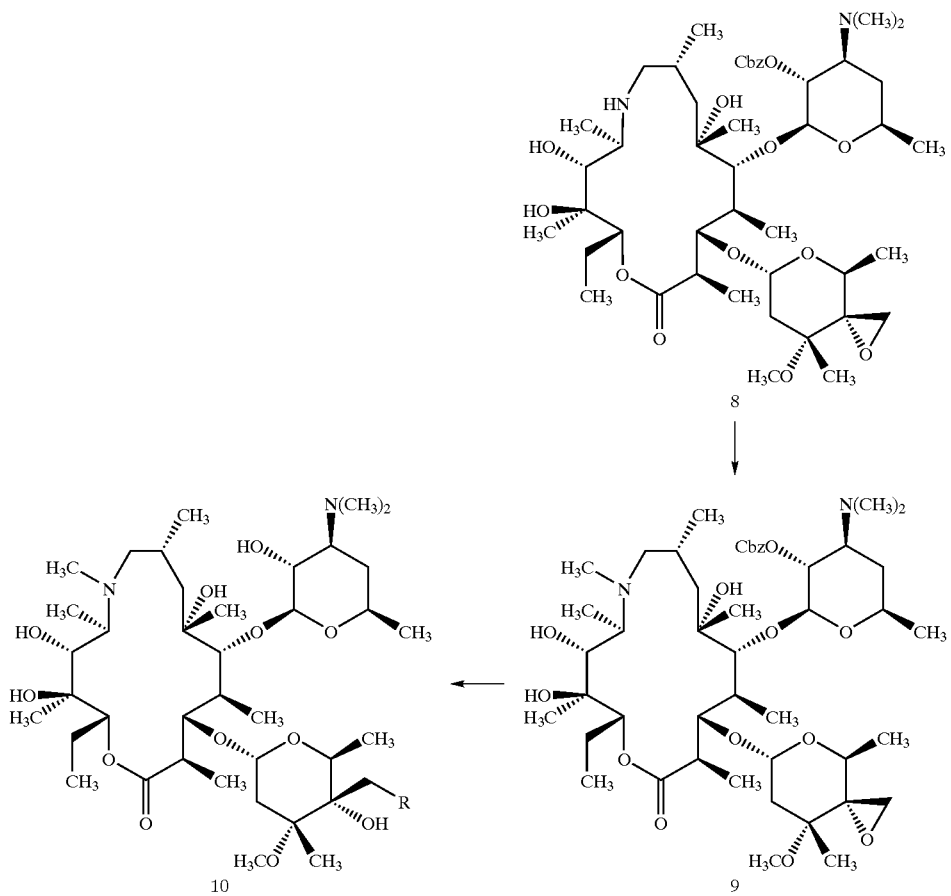

EXAMPLE 34

Following the procedure of Example 31, 4"-deoxy-4"-oxo-9-deoxo-9a-aza-9a-methyl-9a-homoerythromycin A (494 mg, 0.662 mmol) and benzylmagnesiumchloride (4.4 ml, 4.4 mmol, 1.0 M THF solution) were reacted to generate the compound for formula 7 wherein R is benzyl, 30 mg (0.172 mmol, 5.4% yield): FABMS: m/e 839 (MH$^+$).

EXAMPLE 35

To a solution of 4"-deoxy-4"-oxo-9-deoxo-9a-aza-9a-methyl-9a-homoerythromycin A (602 mg, 0.806 mmol) in chloroform (8 ml) was added TMSCN (220 ml, 1.64 mmol) followed by ZnI$_2$ (13 mg, 0.04 mmol). The reaction mixture was stirred at room temperature for 30 minutes. A solution of 10% K$_2$CO$_3$ in water (10 ml) was added. The organic layer was washed with brine, dried (MgSO$_4$) and concentrated in vacuo to afford the crude product. Chromatography The compound of formula 8, referred to in the scheme above, (20.0 g, 22.7 mmol) was dissolved in chloroform (150 ml), followed by the addition of formaldehyde (5.1 mL 37% solution 68.1 mmol) and formic acid (2.8 mL, 74.9 mmol). The resulting solution was heated to 60° C. overnight to provide the compound of formula 9. The reaction mixture was poured into water (150 mL) and methylene chloride (50 mL). The organic layer was washed with water (150 mL) one more time, and the aqueous layers were combined, and the pH of the solution was adjusted to 9 by the addition of 5N NaOH solution. The product was then extracted with methylene chloride (3×100 mL). The combined organic layers were washed with brine, dried over sodium sulfate, and the organic solvent was removed in vacuo to give the compound of formula 9 (19.6 g, 96%). MS (TS) m.·.z 895.

1–2 g of the compound of formula 9 was dissolved in methanol (10 mL), followed by the addition of KI (10 eq.) and an amine corresponding to the R groups referred to in Table 2 below (10 eq.). After the reaction time indicated below, the reaction mixture was diluted with water (10 mL) and extracted with $CH_2Cl_2$ (3×15 mL). The combined organic layers were washed with brine, dried with $Na_2SO_4$, filtered and purified by flash chromatography, to provide the compounds of formula 10 with the R groups indicated in Table 2 below.

TABLE 2

| Example | R | Reaction Time (hours) | Yield (%) | Mass Spec |
|---|---|---|---|---|
| 36 | allyamino | 24 | 29 | 818 |
| 37 | propylamino | 48 | 42 | 820 |
| 38 | isopropylamino | 72 | 44 | 820 |
| 39 | cyclopropylamino | 48 | 33 | 818 |
| 40 | isobutylamino | 48 | 43 | 834 |
| 41 | sec-butylamino | 72 | 38 | 834 |
| 42 | dimethylamino | 24 | 35 | 806 |
| 43 | trimethyleneimino | 24 | 30 | 818 |
| 44 | butylamino | 48 | 34 | 834 |
| 45 | diethyamino | 168 | 44 | 834 |
| 46 | ethylamino | 48 | 31 | 806 |
| 47 | N-ethylmethylamino | 48 | 36 | 820 |
| 47(a) | pyrrolidino | 96 | 60 | 832.7 |
| 47(b) | piperidino | 96 | 60 | 846.7 |
| 47(c) | 3,4-difluorobenzylamino | 48 | 18.7 | 904.8 |
| 47(d) | 4-methoxybenzyl-amino | 48 | 17.1 | 898.5 |
| 47(e) | 4-trifluoromethylbenzyl-amino | 48 | 44.8 | 936.7 |
| 47(f) | anilino | 120 | 31 | 865.7 |
| 47(g) | 4-fluorobenzylamino | 60 | 30 | 886.7 |
| 47(h) | 3-fluorobenzylamino | 48 | 42.8 | 886.7 |
| 47(i) | 2-fluorobenzylamino | 48 | 55.8 | 886.7 |
| 47(j) | 2,4-difluorobenzylamino | 48 | 41.4 | 904.1 |
| 47(k) | 2,5-difluorobenzylamino | 48 | 33.7 | 904.1 |
| 47(l) | 3,5-difluorobenzylamino | 48 | 44.4 | 904.1 |
| 47(m) | 1-(4-fluorophenyl)piperazine | 48 | 25.9 | 941.1 |
| 47(n) | 2-trifluoromethylbenzyl-amino | 48 | 41.6 | 936.1 |
| 47(o) | 4-trifluoromethoxybenzyl-amino | 48 | 39.7 | 952.1 |
| 47(p) | 3-trifluoromethoxybenzyl-amino | 48 | 38.3 | 936.1 |
| 47(q) | 2-fluorophenylethyl-amino | 48 | 31.2 | 900.2 |
| 47(r) | 3-fluorophenylethyl-amino | 48 | 25.5 | 900.2 |
| 47(s) | 4-pyridylmethylamino | 48 | 37.9 | 869.6 |
| 47(t) | (methyl)(3-pyridylmethyl)amino | 72 | 11 | 883.5 |
| 47(u) | 4-hydroxy-3-methoxybenzyl-amino | 48 | 8 | 914.1 |
| 47(v) | piperonylamino | 48 | 25 | 912.1 |
| 47(w) | 3-methoxybenzyl-amino | 48 | 24 | 898.1 |
| 47(x) | 2-methoxybenzyl-amino | 48 | 25 | 898.5 |
| 47(y) | 4-fluorophenylethyl-amino | 48 | 62 | 900.1 |
| 47(z) | 3-pyridylmethylamino | 48 | 30.5 | 869.3 |
| 47(aa) | 2-pyridylmethylamino | 48 | 49.9 | 869.3 |
| 47(ab) | benzylamino | 48 | 28 | 868.6 |

The following scheme illustrates the preparation of compounds referred to in Examples 48–49 below.

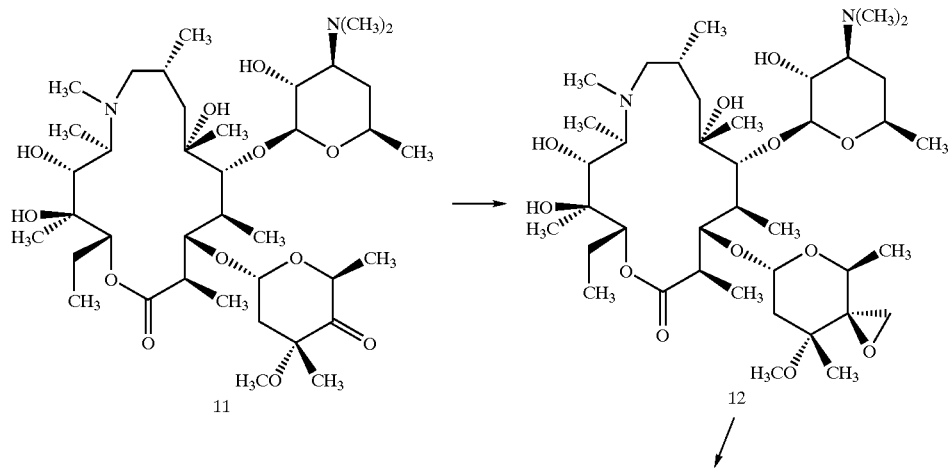

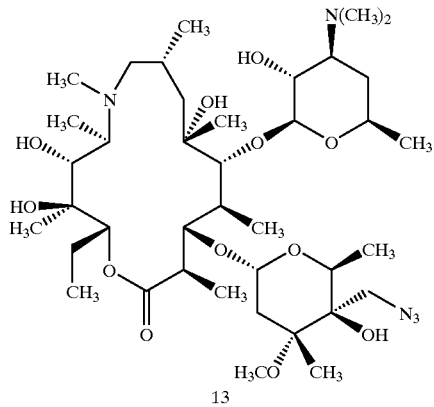

13

EXAMPLE 48

To a solution of sodium hydride (41.5 mg, 1.73 mmol) in DMF (5 ml) was added trimethylsulfoxonium iodide (399 mg, 1.77 mmol). After 15 minutes, the slurry reaction mixture became clear. A solution of 4"-deoxy-4"-oxo-9-deoxo-9a-aza-9a-methyl-9a-homoerythromycin A (940 mg, 1.26 mmol) in DMSO (3 ml) was added slowly. The resulting yellow solution was stirred for 15 minutes at room temperature and 45 minutes at 55° C., and then at room temperature overnight. The reaction mixture was taken into water (20 ml) and ethyl acetate (20 ml): The organic layer was washed with brine, dried (MgSO$_4$) and concentrated to afford the crude product which was chromatographed on silica gel (CHCl$_3$—MeOH—NH$_4$OH (97/3/0.1)) to give the above compound of formula 12 as a white solid, 362 mg (0.476 mmol, 38% yield): FABMS: m/e 761 (MH$^+$).

EXAMPLE 49

To a solution of the compound prepared in Example 48 (95 mg, 0.12 mmol) in 9 ml of MeOH—H$_2$O (8/1) was added sodium azide (39 mg, 0.60 mmol) followed by NH$_4$Cl (19 mg, 0.36 mmol). The reaction mixture was heated at 80° C. for 24 hours. Methanol was removed in vacuo on a rotary evaporator. The product mixture was taken into ethyl acetate (15 ml) and H$_2$O (15 ml). The aqueous layer, after separation, was extracted with ethyl acetate (15 ml). The combined organic extracts were washed with brine, dried over magnesium sulfate and concentrated to afford the compound of formula 13 as a white solid, 90 mg (0.11 mmol, 93% yield): (FABMS: m/e 804 (MH$^+$).

The following scheme illustrates the preparation of compounds referred to in Examples 50–54 below.

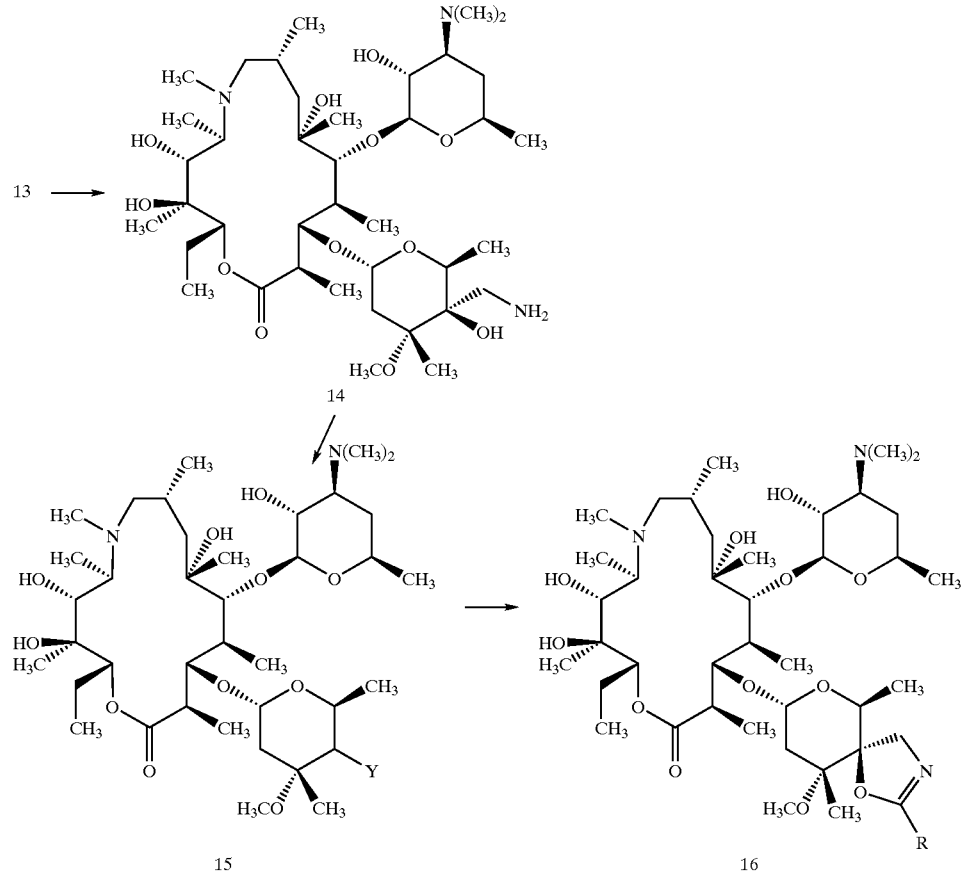

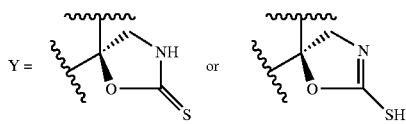

EXAMPLE 50

To a solution of the compound prepared in Example 49 (709 mg, 0.882 mmol) was added Pd (10% on carbon) powder (94 mg, 0.088 mmol). The slurry was stirred under $H_2$ (1 atm) for 18 hours. The reaction mixture was filtered through Celite™. Evaporation of the filtrate afforded the compound of formula 14 as a white solid, 670 mg (0.88 mmol, 100% yield): FABMS: m/e 778 (MH+).

EXAMPLE 51

To a solution of the compound prepared in Example 50 (163 mg, 0.209 mmol) in $CH_2Cl_2$ (10 ml) at 0° C. was added thiocarbonyldiimidazole (43 mg, 0.242 mmol). The ice bath was removed and the reaction mixture was stirred at ambient temperature overnight. The solvent was removed. The product mixture was taken in ethyl acetate and water. The organic layer was washed with 5% $K_2CO_3$ solution and then brine, dried over magnesium sulfate and concentrated to afford the compound of formula 15 as a white solid, 170 mg (0.207 mmol, 99% yield).

The compound of formula 15 (168 mg, 0.205 mmol) was dissolved in acetone (6 ml) followed by the addition of 3,4-dichlorophenacyl bromide (63 mg, 0.234 mmol) and sodium bicarbonate (38 mg, 0.417 mmol). The reaction mixture was stirred at ambient temperature for 20 hours. The organic solvent was removed. The product mixture was taken into ethyl acetate and was washed with 5% $K_2CO_3$, brine, dried over magnesium sulfate and concentrated to afford the crude product. Chromatography on silica gel ($CHCl_3$—MeOH—$NH_4OH$=98/2/0.1) gave the compound of formula 16 wherein R is as provided below as a white solid, 90 mg (0.09 mmol, 44% yield): FABMS: m/e 1006 (MH+).

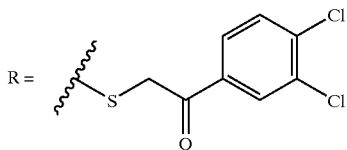

EXAMPLE 52

To a solution of the compound of formula 15 (225 mg, 0.274 mmol) in anhydrous methanol (10 ml) was added sodium methoxide (50 mg, 0.926 mmol). The solution was stirred for 10 minutes and cooled to 0° C. Methyl iodide (60 ml, 0.99 mmol) was added dropwise. The reaction mixture was warmed to room temperature and stirred at ambient temperature for 7 hours. The organic solvent was removed. The product mixture was taken into ethyl acetate and was washed with 5% $K_2CO_3$, brine, dried over magnesium sulfate and concentrated to afford the crude product. Chromatography on silica gel ($CHCl_3$—MeOH—$NH_4OH$=97/3/0.1) gave the compound of formula 16 wherein R is methylthio as a white solid, 231 mg (0.277 mmol, 36% yield): FABMS: m/e 834 (MH+).

EXAMPLE 53

To a solution of the compound of formula 14 (250 mg, 0.321 mmol) in dichloroethane (10 ml) was added ethyl 2-thiophenecarboximidate hydrochloride (72 mg, 0.461 mmol), which was prepared via bubbling HCl gas through a benzene solution of 2-thiophene carbonitrile and ethanol (1.1 equivalent) for 2 hours and stirring at ambient temperature overnight. The slurry reaction mixture became clear upon addition of triethyl amine (65 ml, 0.467 mmol). It was refluxed overnight. The product mixture was taken into ethyl acetate and water, and the pH was adjusted to 1.9 with 10% HCl solution. The aqueous layer was adjusted to pH 9.5 and extracted with ethyl acetate. The organic extract was washed with brine, dried over magnesium sulfate and concentrated to afford the crude product. Chromatography on silica gel ($CHCl_3$—MeOH—$NH_4OH$=99/1/0.1) gave the compound of formula 16 wherein R is 2-thienyl as a white solid, 92 mg (0.106 mmol, 33% yield): FABMS: m/e 870 (MH+).

EXAMPLE 54

$ZnCl_2$ (2 mg) was placed in a round bottom flask and heated to melt under vacuum. After cooled to room temperature, a solution of the compound of formula 14 (236 mg, 0.303 mmol) and 2-cyanopyridine( 49 mg, 0.467 mmol) in chlorobenzene (10 ml) was added. The reaction mixture was heated to reflux overnight. Water was added and adjusted to pH 2. After separation, the aqueous layer was adjusted to pH 9.5 and extracted with ethyl acetate. The organic extract was washed with brine, dried over magnesium sulfate and concentrated to afford the crude product. Chromatography on silica gel ($CHCl_3$—MeOH—$NH_4OH$=98/2/0.1) gave the compound of formula 16 wherein R is 2-pyridyl as a white solid, 47 mg (0.054 mmol, 18% yield): FABMS: m/e 865 (MH+).

EXAMPLE 55

To a solution of the compound of formula 14 (383 mg, 0.492 mmol) in methanol (5 ml) was added to a solution of cyanogen-bromide (57 mg, 0.538 mmol) and sodium acetate (90 mg, 1.097 mmol) in methanol (5 ml) dropwise. The reaction mixture was stirred at ambient temperature overnight. The solvent was evaporated and the solid was taken into ethyl acetate and water, and the pH was adjusted to pH 9.5 with 10% $K_2CO_3$ solution. The organic extract was washed with brine, dried over magnesium sulfate and concentrated to afford the crude product. Chromatography on silica gel ($CHCl_3$—MeOH—$NH_4OH$=96/4/0.1) gave the compound of formula 16 wherein R is amino as a white solid, 124 mg (0.155 mmol, 31% yield): FABMS: m/e 803 (MH+).

The following scheme illustrates the preparation of compounds referred to in Examples 58–63 below.

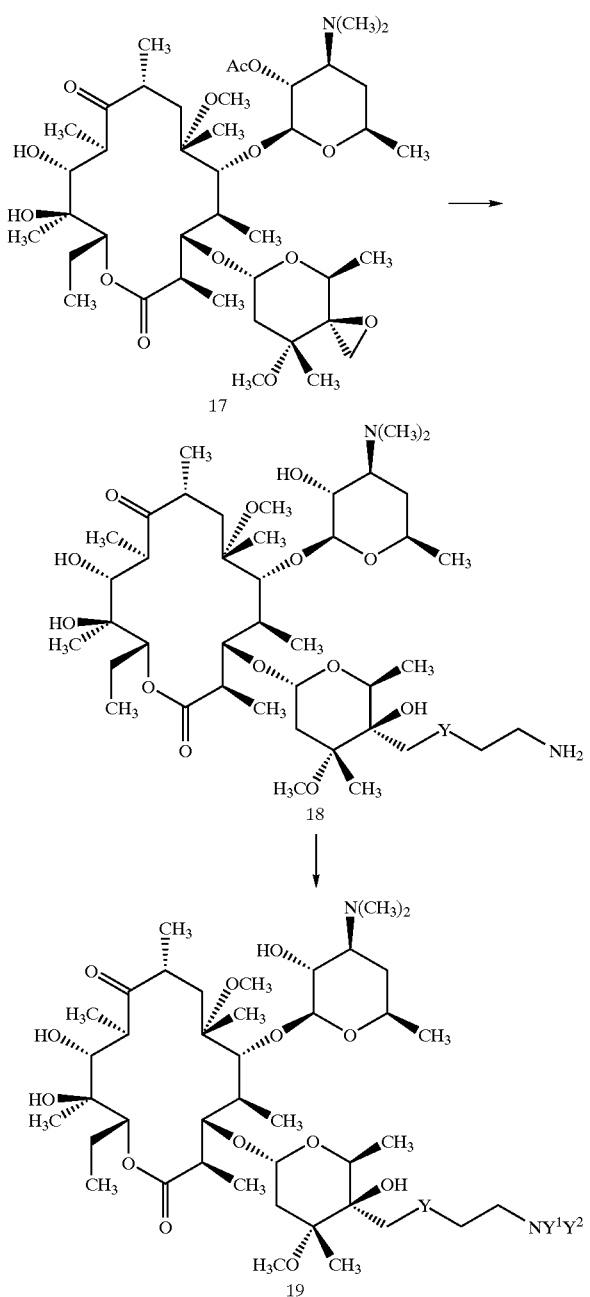

EXAMPLE 56

A solution of the compound of formula 17 (3 g, 3.7 mmol) in 30 mL of MeOH was heated at 50° C. overnight with 2.25 g (37.5 mmol) of ethylenediamine and 6.21 g (37.1 mmol) of potassium iodide. MeOH was evaporated from the resulting mixture, and the residue was dissolved in $CH_2Cl_2$ and washed with brine. After drying over $Na_2SO_4$, $CH_2Cl_2$ was evaporated under reduced pressure. The residue was chromatographed on $SiO_2$ (5% MeOH—$CH_2Cl_2$—0.5% $NH_4OH\rightarrow 10\%$ MeOH—$CHCl_2$-1%$NH_4OH$) to give 2.72 (89%) of the compound of formula 18 wherein Y is —NH—: MS m/e 821 (M+1).

EXAMPLE 57

A solution of the compound prepared in Example 56 (1.0 g, 1.2 mmol), o-anisaldehyde (174 mg, 1.3 mmol) and sodium acetate (100 mg, 1.2 mmol) in 20 mL of $CH_2Cl_2$ was stirred at room temperature for 1 hour. To this solution were added 388 mg (1.8 mmol) of sodium triacetoxyborohydride. After 2.5 hour of stirring at room temperature, the reaction mixture was diluted was $CH_2Cl_2$ and washed with a saturated $NaHCO_3$ solution and brine. After drying over $Na_2SO_4$, the organic solvent was removed. The reside was chromatographed twice on $SiO_2$ (2% MeOH—$CH_2Cl_2$—0.2% $NH_4OH$). The material was further purified by preparative $SiO_2$ plates (10% MeOH—$CH_2Cl_2$-1% $NH_4OH$) to give 660 mg (58%) of the compound of formula 19 wherein Y is —NH—, $Y^1$ is H, and $Y^2$ is 2-methoxybenzyl: MS m/e 940 (M+1).

EXAMPLES 58–59

In methods analogous to that of Example 57, by replacing o-anisaldehyde with p-trifluoromethylbenzaldehyde and p-phenoxybenzaldehyde the compounds of Examples 58 and 59, respectively, were generated wherein said compounds had the general structure of formula 19 and Y and $Y^1$ are as defined for the compound of Example 57 and $Y^2$ is as provided below.

| Example | $Y^2$ | Mass Spec | Yield |
|---|---|---|---|
| 58 | 4-trifluoromethylbenzyl | 978 (M + 1) | 33% |
| 59 | 4-phenoxybenzyl | 1002 (M + 1) | 46% |

EXAMPLE 60

A solution of the compound prepared in Example 57 above (468 mg, 0.5 mmol), isobutyraldehyde (36 mg, 0.5 mmol), and sodium acetate (42 mg, 0.5 mmol) in 5 mL of $CH_2Cl_2$ was stirred at room temperature for 1.5 hour. To this solution were added 164 mg (0.77 mmol) of sodium triacetoxyborohydride. After stirring at room temperature for 0.5 hr, the reaction mixture was diluted with $CH_2Cl_2$ and washed with a $NaHCO_3$ solution and brine. After drying over $MgSO_4$, the solvent was removed under reduced pressure. The residue was chromatographed on $SiO_2$ (4% MeOH—$CH_2Cl_2$-0.4% $NH_4OH$) to give 256 mg (51%) of the compound of formula 19 wherein Y is —NH—, $Y^1$ is 2-methylpropyl, and $Y^2$ is 2-methoxybenzyl: MS m/e 996 (M+1).

EXAMPLE 61

A solution of the compound of formula 20 (522 mg, 0.65 mmol), 2-phthalimidoethanethio (1.08 g, 5.2 mmol) and potassium iodide (865 mg, 5.2 mmol) in 5 mL of MeOH was heated under $N_2$ for 48 hours. MeOH was then removed under reduced pressure, and the residue was dissolved in $CH_2Cl_2$ and washed with a $NaHCO_3$ solution and brine. After drying over $MgSO_4$, $CH_2Cl_2$ was removed under reduced pressure. The residue obtained was dissolved in 10 mL of EtOH and treated with 7.5 mL of hydrazine hydrate. After stirring at room temperature for 3 hours EtOH was removed under reduced pressure, and the residue was extracted with $CH_2Cl_2$. The organic layer was washed with brine and dried over $MgSO_4$. A $SiO_2$ chromatography of the residue (4% MeOH— $CH_2Cl_2$ -0.4% $NH_4OH\rightarrow 5\%$ MeOH—$CH_2Cl_2$-0.5% mH4OH) gave 287 mg (53%) of the compound of formula 18 wherein Y is S: MS m/e 837 (M+1).

EXAMPLE 62

In a method analogous to that of Example 57 and starting with the compound of Example 60, a compound of the formula 19 wherein Y is S, $Y^1$ and $Y^2$ are both 2-methoxybenzyl (70% yield, MS m/e 957 (M+1)) and a compound of formula 19 wherein Y is S, $Y^1$ is H, and $Y^2$ is 2-methoxybenzyl (3% yield, MS m/e 1077 (M+1)) were obtained.

EXAMPLE 63

In a method analogous to that of Example 60 and starting with the compound of formula 19 wherein Y is S, $Y^1$ is H, and $Y^2$ is 2-methoxybenzyl, and propionaldehyde, the compound of formula 19 wherein Y is S, $Y^1$ is n-propyl, and $Y^2$ is 2-methoxybenzyl was obtained in 70% yield, MS m/e 999 (M+1).

The following scheme illustrates the preparation of compounds referred to in Examples 64–72 below.

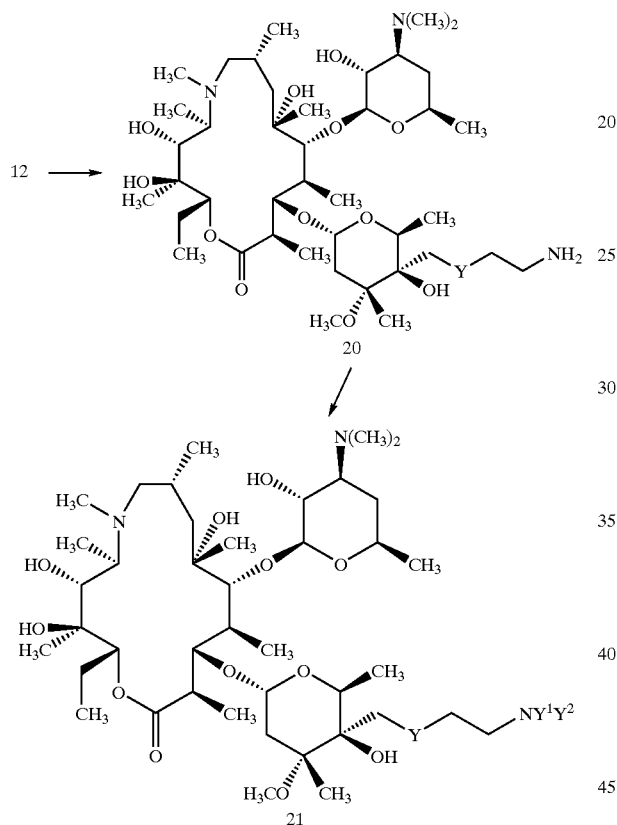

EXAMPLE 64

Starting with the compound of formula 12, the compound of formula 20 was prepared wherein Y=NH using a procedure analogous to the procedure described in Example 56 in 35% yield; MS m/e 821 (M+1).

EXAMPLE 65

Using a procedure analogous to that described in Example 63 and starting with the product of Example 64, the compound of formula 21 was obtained wherein Y is NH, $Y^1$ is H, and $Y^2$ is 2-methoxybenzyl, in 16% yield; MS m/e 942 (M+1).

EXAMPLE 66

Using a procedure analogous to that described in Example 63 and starting with the product of example 64 and p-trifluoromethylbenzaldehyde, the compound of formula 21 was obtained wherein Y is NH, $Y^1$ is H, and $Y^2$ is 4-trifluoromethylbenzyl, in 18% yield; MS m/e 980 (M+1).

EXAMPLE 67

A solution of the product from Example 64 (145 mg, 0.18 mmol) and o-anisaldehyde (122 mg, 0.9 mmol) in 10 mL of EtOH was stirred overnight at room temperature. EtOH was removed under reduced pressure and the residue was dissolved in 5 mL of MeOH. Sodium borohydride (34 mg, 0.9 mmol) was added and the mixture was stirred at room temperature for 2 hours. MeOH was removed under reduced pressure and the residue was dissolved in $CH_2Cl_2$ and washed with water and brine. The organic layer was dried over $Na_2SO_4$ and evaporated. A $SiO_2$ chromatography (5% MeOH—$CH_2Cl_2$-0.2% $NH_4OH$) of the residue gave 104 mg (54%) of the compound of formula 21 wherein Y is NH, and $Y^1$ and $Y^2$ are 2-methoxybenzyl, title compound; MS m/e 1061 (M+1).

EXAMPLE 68

Following a procedure analogous to that of Example 61, the compound of formula 20 was obtained where in Y is S, in 63% yield; MS m/e 838 (M+1).

EXAMPLE 69

Following a procedure analogous to that of Example 57, the compound of formula 21 was prepared where Y is S, $Y^1$ is H, and $Y^2$ is 2-methoxybenzyl, in 28% yield; MS m/e 958 (M=1).

EXAMPLE 70

A solution of the product from Example 64 (80 mg, 0.1 mmol) o-anisaldehyde (126 mg, 1 mmol), sodium acetate (64 mg, 0.78 mmol), and sodium triacetoxyborohydride (64 mg, 0.3 mmol) was stirred overnight at room temperature. The resulting solution was distilled with $CH_2Cl_2$ and washed with a saturated $Na_2CO_3$ solution and brine. The organic layer was dried over $K_2CO_3$ and evaporated. The residue was chromatographed on $SiO_2$plate (2.5% MeOH-methyl t-butylether-2.5% triethylamine) to give 20 mg (19%) of the compound of formula 21 was prepared wherein Y is S, and $Y^1$and $Y^2$ are 2-methoxybenzyl, MS m/e 1078 (M+1).

EXAMPLE 71

A solution of the product from Example 70 (31 mg, 0.03 mmol) formaldehyde (37% aqueous solution, 83 μL, 1 mmol), and formic acid (18 μL, 0.47 mmol) in 2mL of $CHCl_3$ was heated at 61° C. for 1 hr. The reaction mixture was diluted with $CH_2Cl_2$ and wash with a saturated solution of $NaHCO_3$ and brine. After drying over $K_2CO_3$, the solvents were removed under reduced pressure. The residue was chromatographed on a $SiO_2$ plate (5% MeOH—$CH_2Cl_2$-2.5% triethylamine) to give 14 mg (45%) of the compound of formula 21 wherein Y is S, $Y^1$ is methyl, and $Y^2$ is 2-methoxybenzyl; MS m/e 972 (M+1).

EXAMPLE 72

A solution of the compound of formula 12 (380 mg, 0.5 mmol) and magnesium perchlorate (223 mg, 1 mmol) in 5 mL of MeOH was refluxed under $N_2$ for 9 days. MeOH was removed under reduced pressure and the residue was dissolved in $CH_2Cl_2$ and washed with water and brine. The residue was chromatographed on $SiO_2$ (2.5% MeOH—$CH_2Cl_2$-0.5% $NH_4OH$) to give 25 mg (6%) of the configuration indicated below (MS m/e 793 (M+1)):

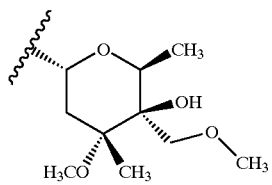

The following scheme illustrates the preparation of compounds referred to in Examples 73–75 below.

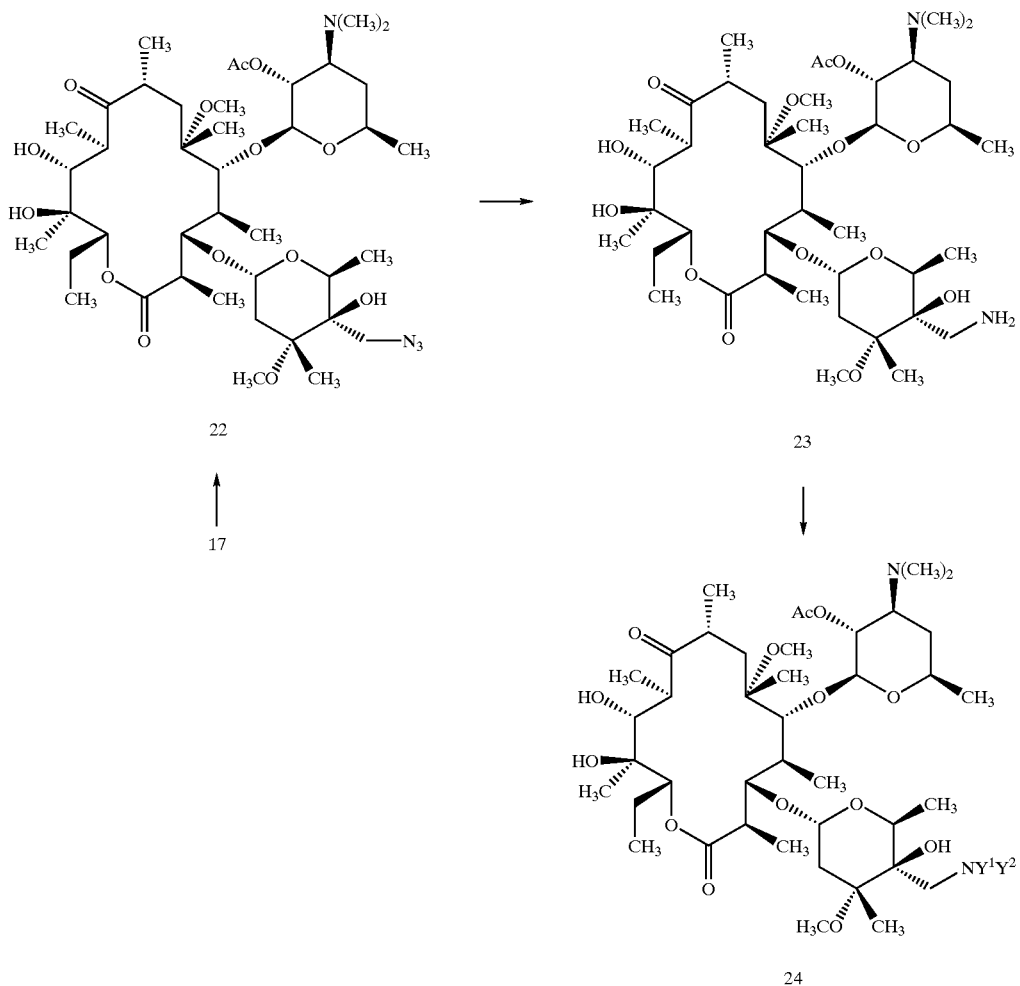

EXAMPLE 73

A solution of the compound of formula 17 (500 mg, 0.62 mmol), sodium azide (90 mg, 1.23 mmol), and lithium perchlorate (135 mg, 1.27 mmol) in 5 mL of acetonitrile was refluxed for 4 days. After evaporation of acetonitrile the residue was dissolved in $CH_2Cl_2$ and washed with water and brine. The $CH_2Cl_2$ layer was dried over $MgSO_4$ and concentrated. The residue was dissolved in 5 mL of MeOH and refluxed overnight. The residue obtained after evaporation of the solvent was chromatographed on $SiO_2$ (4% MeOH—$CH_2Cl_2$-0.4% $NH_4OH$) to give 218 mg (44%) of the compound of formula 22; m/e 803 (M+1).

EXAMPLE 74

A solution of the compound of formula 23 (250 mg, 0.311 mmol) in 15 mL of EtOH was hydrogenated in the presence of 30 mg 10% Pd/C in a Parr shaker. After 2 hours at room temperature the reaction mixture was filtered through Celite™ and the solvent was removed under reduced pressure. The residue was chromatographed on $SiO_2$ 98% MeOH—$CH_2Cl_2$-0.8% $NH_4OH$) to give 140 mg (58%) of the compound of formula 23; MS m/e 777 (M+1).

EXAMPLE 75

Following a procedure analogous to that of Example 57 and using the compound of formula 26 as a starting material, the compound of formula 24 was prepared where $Y^1$ is H and $Y^2$ is 2-methoxybenzyl, in 43% yield; MS m/e 897 (M+1).

What is claimed is:
1. A compound of the formula:

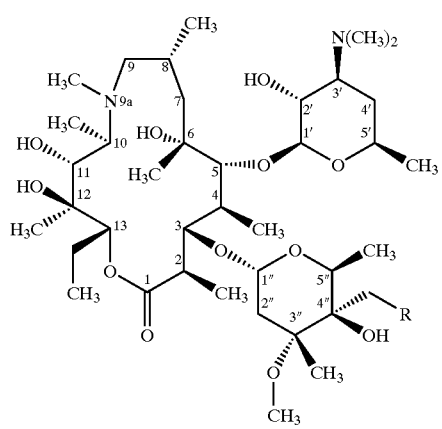

or a pharmaceutically acceptable salt thereof, wherein:

R is selected from the group consisting of n-butylamino, propylamino, methoxyethylamino, dimethylamino, cyclopropylamino, allylamino, imidazol-1yl, 2,2,2-trifluoroethylamino, bis(2-hydroxyethyl)amino, bis(2-methoxyethyl)amino, 2-hydroxyethylthio, mercapto, 4-methylimidazol-1yl, 2-propynylamino, diallylamino, 1,2,3-triazol-1-yl, 2-methylimidazol-1-yl, 1,2,4-triazol-1yl, n-butylamino, propylamino, dimethylamino, and $C_1$–$C_{10}$ alkyl, $C_1$–$C_{10}$ alkenyl, and $C_1$–$C_{10}$ alkynyl, wherein said alkyl, alkenyl, and alkynyl are optionally substituted by 1 or 2 substituents independently selected from hydroxy, halo and $C_1$–$C_6$ alkyl.

2. A method of preparing a compound of formula 6:

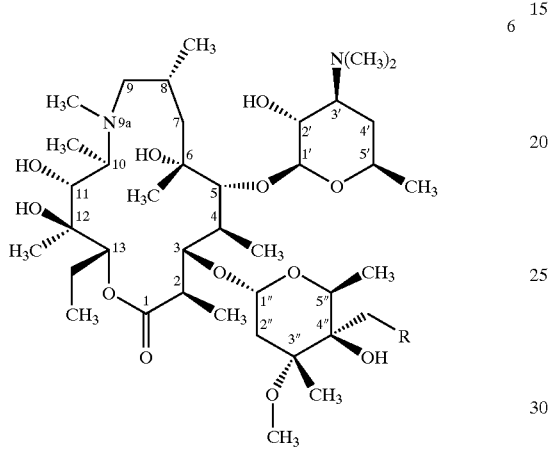

or a pharmaceutically acceptable salt thereof wherein:

R is selected from the group consisting of n-butylamino, propylamino, methoxyethylamino, dimethylamino, cyclopropylamino, allylamino, imidazol-1yl, 2,2,2-trifluoroethylamino, bis(2-hydroxyethyl)amino, bis(2-methoxyethyl)amino, 2-hydroxyethylthio, mercapto, 4-methylimidazol-1-yl, 2-propynylamino, diallylamino, 1,2,3-triazol-1-yl, 2-methylimidazol-1-yl, and 1,2,4-triazol-1yl, which comprises:

(a) dissolving a compound of the formula 3a:

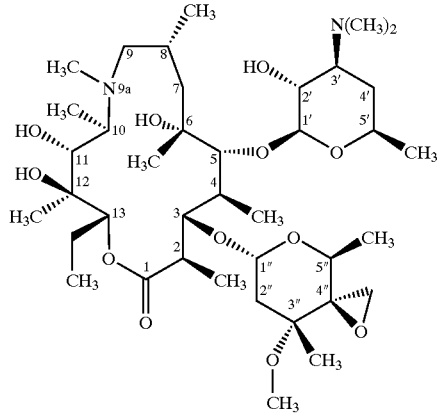

in an amine;

(b) adding a catalytic amount of pyridinium hydrochloride;

(c) heating the solution to 40–75° C.; and (d) quenching with bicarbonate;

wherein the amine corresponds to an amino group selected from the definition of R.

3. The method of claim 2, wherein the temperature in step (c) is from 50–75° C.

4. The method of claim 2, wherein the temperature in step (c) is from 45–50° C.

* * * * *